(12) United States Patent
Urano et al.

(10) Patent No.: US 8,599,369 B2
(45) Date of Patent: Dec. 3, 2013

(54) DEFECT INSPECTION DEVICE AND INSPECTION METHOD

(75) Inventors: Yuta Urano, Yokohama (JP); Shigenobu Maruyama, Oiso (JP); Toshiyuki Nakao, Yokohama (JP); Toshifumi Honda, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/378,418

(22) PCT Filed: Jun. 9, 2010

(86) PCT No.: PCT/JP2010/003826
§ 371 (c)(1),
(2), (4) Date: Jan. 18, 2012

(87) PCT Pub. No.: WO2010/146799
PCT Pub. Date: Dec. 23, 2010

(65) Prior Publication Data
US 2012/0133928 A1   May 31, 2012

(30) Foreign Application Priority Data
Jun. 18, 2009  (JP) .................. 2009-144881

(51) Int. Cl.
*G01N 21/47* (2006.01)
*G01N 21/55* (2006.01)

(52) U.S. Cl.
USPC ..................... 356/237.2; 356/237.5

(58) Field of Classification Search
USPC ................. 356/237.1–237.5, 394
See application file for complete search history.

(56) References Cited

U.S. PATENT DOCUMENTS

| | | | |
|---|---|---|---|
| 5,903,342 A | 5/1999 | Yatsugake et al. | |
| 6,587,192 B2 * | 7/2003 | Isozaki et al. | 356/237.2 |
| 6,608,676 B1 | 8/2003 | Zhao et al. | |
| 7,385,688 B1 | 6/2008 | Kadkly et al. | |
| 7,710,557 B2 * | 5/2010 | Oshima et al. | 356/237.5 |
| 2003/0020904 A1 | 1/2003 | Uto et al. | |
| 2005/0185172 A1 | 8/2005 | Ishimaru et al. | |
| 2006/0256325 A1 | 11/2006 | Mcmillan et al. | |
| 2008/0013084 A1 * | 1/2008 | Matsui et al. | 356/237.5 |
| 2008/0297783 A1 | 12/2008 | Urano et al. | |

(Continued)

FOREIGN PATENT DOCUMENTS

| | | |
|---|---|---|
| JP | 6-258233 | 9/1994 |
| JP | 9-304289 | 11/1997 |

(Continued)

*Primary Examiner* — Sang Nguyen
(74) *Attorney, Agent, or Firm* — Antonelli, Terry, Stout & Kraus, LLP.

(57) ABSTRACT

A defect inspection method wherein illumination light having a substantially uniform illumination intensity distribution in a certain direction on the surface of a specimen is radiated onto the surface of the specimen; wherein multiple components of those scattered light beams from the surface of the specimen which are emitted mutually different directions are detected, thereby obtaining corresponding multiple scattered light beam detection signals; wherein the multiple scattered light beam detection signals is subjected to processing, thereby determining the presence of defects; wherein the corresponding multiple scattered light detecting signals is processed with respect to all of the spots determined to be defective by the processing, thereby determining the sizes of defects; and wherein the defect locations on the specimen and the defect sizes are displayed with respect to all of the spots determined to be defective by the processing.

15 Claims, 21 Drawing Sheets

(56) References Cited

U.S. PATENT DOCUMENTS

| | | |
|---|---|---|
| 2009/0213366 A1 | 8/2009 | Nakano et al. |
| 2009/0257058 A1* | 10/2009 | Urano et al. .................. 356/364 |
| 2009/0279081 A1 | 11/2009 | Urano et al. |
| 2009/0290168 A1* | 11/2009 | Hamamatsu et al. ......... 356/600 |
| 2009/0323051 A1 | 12/2009 | Matsui |

FOREIGN PATENT DOCUMENTS

| | | |
|---|---|---|
| JP | 2000-105203 | 4/2000 |
| JP | 2003-42967 | 2/2003 |
| JP | 2004-177284 | 6/2004 |
| JP | 2005-337851 | 12/2005 |
| JP | 2006-501469 | 1/2006 |
| JP | 2006-201179 | 8/2006 |
| JP | 2007-33433 | 2/2007 |
| JP | 2007-309713 | 11/2007 |
| JP | 2008-8803 | 1/2008 |
| JP | 2008-268141 | 11/2008 |
| JP | 2009-236791 | 10/2009 |
| WO | WO 2004/031753 A1 | 4/2004 |

* cited by examiner

SCHEMATIC VIEW ILLUSTRATING DISTRIBUTION OF ILLUMINATION INTENSITY AT SPECIMEN SURFACE

FIG. 16
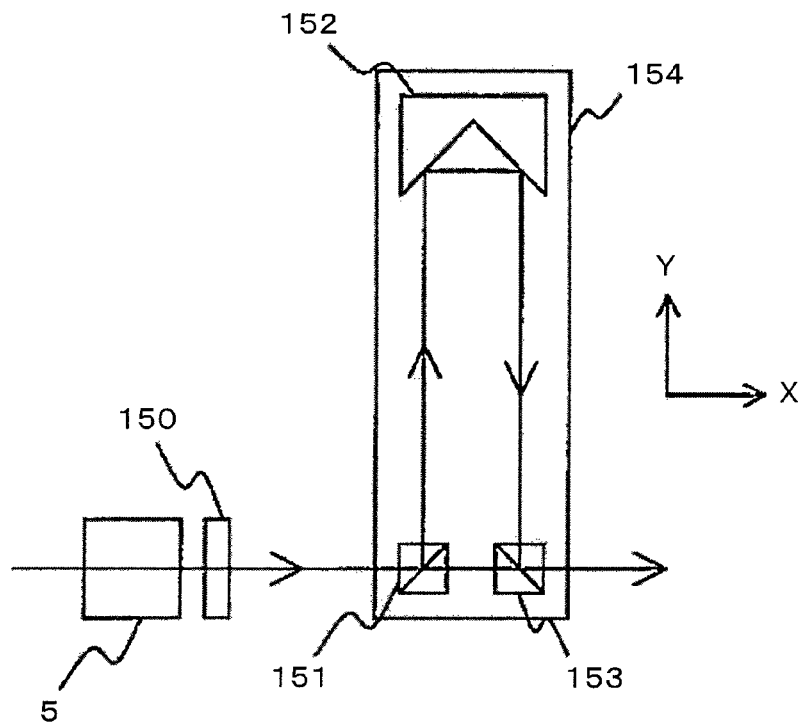
FIG. 17
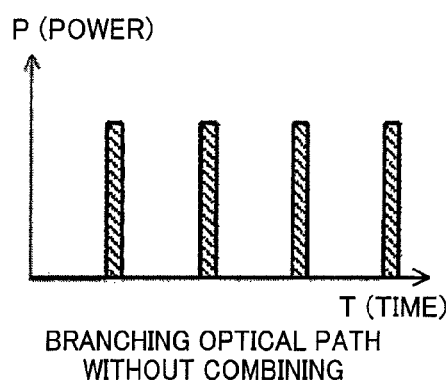
BRANCHING OPTICAL PATH
WITHOUT COMBINING
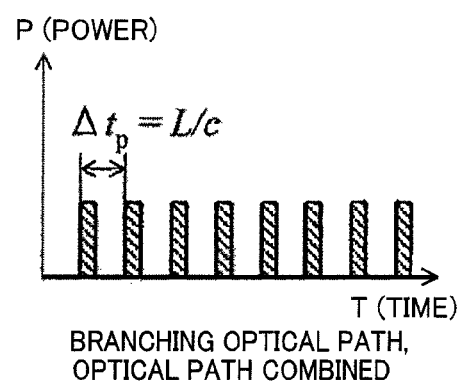
BRANCHING OPTICAL PATH,
OPTICAL PATH COMBINED

DEFECT INSPECTION DEVICE AND INSPECTION METHOD

BACKGROUND ART

The present invention relates to a defect inspection method and inspection device used to inspect microscopic defects present on a specimen surface and determine, output the kinds and sizes of defects.

At manufacturing lines for semiconductor substrates or thin-film substrates or the like, defects on the surface of a semiconductor substrate or thin-film substrate or the like are inspected to maintain/improve product yields. Known conventional techniques relating to defect inspection include those disclosed in, for example, Japanese Patent Application Publications JP-A-1997-304289 (Patent Document 1), JP-A-2006-201179 (Patent Document 2), and US Patent Application No. 2006/0256325 (Patent Document 3). In these conventional techniques, in order to detect microscopic defects, the surface of a specimen is irradiated with illumination light focused to a size of tens of micrometers (μm). The scattered light from each defect is focused and detected, thereby inspecting defects with a size measuring between tens of nanometers (nm) and tens of micrometers (μm) or larger. A stage holding the specimen (target substance) can be moved rotationally and translationally to helically scan the surface of the specimen and inspect the entire surface of the specimen.

Patent Documents 1 and 2 also describe techniques that detect high-angle emission components and low-angle emission components of the scattered light from defects to classify the defects based on the ratio between the two.

Patent Document 2 also describes a technique for calculating dimensions of a detected defect based on the intensity of the scattered light from the defect.

Patent Document 3 also describes a technique, for reducing thermal damage to the specimen, that controls power of illumination light, a scanning speed of the illumination spot, or a size of the illumination spot during the inspection of the intended surface. More specifically, the technique assumes that the thermal damage to the specimen is determined by a product of a density and irradiation time of the irradiating illumination power. In order to keep the product lower than a fixed value, the power of the illumination light, the scanning speed of the illumination spot, or the size of the illumination spot is changed in accordance with the radial position on the specimen under scanning.

In addition, U.S. Pat. No. 6,608,676 (Patent Document 4) discloses a technique for inspecting an entire surface of a specimen within a short time. A unidirectionally long gaussian beam is used to illuminate a broad region of the specimen and the entire illuminated region is detected at one time by a multi-pixel detector such as a CCD.

Furthermore, U.S. Pat. No. 7,385,688 (Patent Document 5) discloses a technique that uses a non-spherical lens or a diffractive optical element in off-axis illumination so that illumination light is shaped into an array of illumination spots on the surface of a target object.

CITATION LIST

Patent Literature

Japanese Patent Laid-Open Number 1997-304289
Japanese Patent Laid-Open Number 2006-201179
US Publication Number 2006/0256325
U.S. Pat. No. 6,608,676
U.S. Pat. No. 7,385,688

SUMMARY OF INVENTION

Technical Problem

The defect inspection used in manufacturing processes for semiconductors and/or the like is required to be able to detect microscopic defects, measure detected defect sizes with high accuracy, inspect the specimen non-destructively (or without transmuting the specimen), constantly obtain definite inspection results (counts, positions, sizes, and kinds of the detected defect) for one specimen, inspect a number specimens within a certain time, and more.

In the techniques described in Patent Documents 1, 2, 4, and 5, defects of sizes smaller than 20 nm, in particular, cannot be detected since the scattered light from the defect is very weak and is covered with noise of the scattered light on the surface of the specimen, noise of a detector, or noise of a detection circuit. If the illumination power is raised to avoid this, a temperature of the specimen would be significantly increased by the illumination light and the specimen may be thermally damaged. If the scanning speed for specimens is lowered to avoid thermal damage, a specimen area or total number of specimens inspectable within a fixed time would decrease. For these reasons, it has been difficult to detect microscopic defects at high speed while avoiding thermal damage.

In addition, when the specimen is scanned helically at a constant rotating speed, the moving speed of the illumination spot is minimal at the center of the specimen. Thus, significant thermal damage is applied to the central region of the specimen. In order to avoid this, for example, scanning may be performed while maintaining a constant linear velocity at a scanning position, or X-Y scanning may be conducted to thereby keep the irradiation time constant irrespective of the scanning position on the specimen. However in the former means, an infinite rotating speed is needed to inspect the central region of the specimen and the inspection of the central region is therefore substantially impossible. The latter means requires time for acceleration/deceleration of the stage in switching directions of main scanning and sub-scanning, and thus requires a long time to inspect whole-surface.

Further, the illumination light intensity distribution at the illumination spot is a gaussian distribution. Intensity of a scattered light signal from a defect, detected according to a relative position of the defect with respect to the illumination spot, thus changes and makes defect detection sensitivity variable and reduces defect size calculation accuracy.

On the other hand, the technique described in Patent Document 3 was intended to reduce thermal damage in the vicinity of the specimen center in comparison with other conventional techniques by changing the illumination power in proportion to the radial position on the specimen. Another aim of the technique was to suppress thermal damage in the vicinity of the specimen center at a level equivalent to that of other conventional techniques, while simultaneously improving defect detection sensitivity at the outer region of the specimen. However, assuming that thermal damage is proportional to the product of the irradiation power and the irradiation time causes the following problems.

Firstly, in the estimation of thermal damage, impacts of heat diffusion from the illumination spot are not considered. The thermal damage is prone to be overestimated especially at the central region of the specimen where the irradiation time is long. Thus, the illumination power at the central region of the specimen has been reduced to a level lower than required and defect detection sensitivity has decreased as a result.

Secondly, to avoid thermal damage to the entire surface of the specimen, it is necessary to define a certain level of the illumination power with respect to a standard where the central region of the specimen, that suffers the most thermal damage, is prevented from thermally damaged. However in rotational scanning, the scanning speed (linear velocity) is zero at the central region of the specimen. A theoretical irradiation time diverges to infinite and the thermal damage cannot be quantitatively estimated with the foregoing assumption, and thus the illumination power cannot be defined. Conversely, to guarantee that no thermal damage at the central region occurs, the illumination power needs to be zero so it is impossible to inspect the central region.

Thirdly, as described in Patent Document 3, changing the illumination power according to the radial position on the specimen makes peak values of the scattered light signal differ according to the position on the specimen, even for defects with same sizes. This may cause inconveniences: for example, defects in the outer circumferential region of the specimen may suffer signal saturation, or the peak value of a defect in the central region may decrease to an undetectable level. These inconveniences may result in the variability of defect detection sensitivity or the decrease in defect size calculation accuracy or the like.

Fourthly, as described in Patent Document 3, when a shape of the illumination spot is dynamically changed according to a radial position on the specimen, an illumination spot shape obtained depends on factors such as individual differences in the optical elements of an upstream illumination optical system or control accuracy. It is difficult to control the shape of the illumination spot accurately and also difficult to control the shapes of illumination spots equivalently between a plurality of devices.

Further, as described in Patent Document 5, when the technique that conducts scanning with an array of illumination spots is applied to helical scanning which is suitable for rapid inspection, a difference in curvature between scanning paths may make the scanning paths of the illumination spots overlap or reverse, depending on the radial position on the specimen. Inspection efficiency or an inspection area per unit time decreases as a result.

Further, as described in Patent Document 5, shaping an illumination spot using a non-spherical lens and a diffractive optical element may cause a slight shift in a position or angle, or a slight disturbance in an intensity distribution or wavefront of the light incident upon the non-spherical lens and the diffractive optical element. The outcoming shapes of the illumination spots would be variable and stable inspection results are difficult to obtain.

Solution to Problem

The present invention disclosed herein to solve the above problems is outlined below.

In a first aspect of the present invention the surface of a specimen is irradiated with illumination light having a substantially uniform illumination intensity distribution in a certain direction on the surface of the specimen. Next, the invention detects, of the light scattered from the surface of the specimen by the irradiation, a plurality of scattered-light components emitted in a plurality of directions different from each other, and obtains a plurality of corresponding scattered-light detection signals. After this, the invention determines existence of defects by processing at least one of the scattered-light detection signals, and further determines sizes of the defects by processing at least one of the scattered-light detection signals corresponding to the sections determined to be defective during the defect existence determination. Finally, the invention displays on a screen a positions of the detected defective sections on the specimen surface, and the defect sizes.

A second aspect of the present invention includes: an illumination light regulating step for conditioning illumination light that has been emitted from a light source to a beam of light having a desired quantity of light, position, beam diameter, and polarization state; an illumination intensity distribution control step for guiding the beam obtained in the illumination light regulating step to a specimen surface at a desired angle of incidence, and for controlling an illumination intensity distribution so that the illumination intensity distribution of light illuminating the surface of the specimen is substantially uniform in a certain direction on the specimen surface; a specimen scanning step for, at a position on the specimen surface where the specimen is irradiated with the illumination light in the illumination intensity distribution control step, moving the specimen in a direction substantially perpendicular to the direction in which the illumination intensity distribution is substantially uniform; a scattered-light detection step for detecting, of the scattered light emitted from the specimen surface in the specimen scanning step, a plurality of scattered-light components emitted in a plurality of directions different from each other, and for outputting a plurality of scattered-light detection signals corresponding to the detected scattered-light components; a defect determining step for determining existence of defects by processing at least one of the scattered-light detection signals obtained in the scattered-light detection step; a defect size determining step for determining sizes of the defects by processing at least one of the scattered-light detection signals corresponding to the sections determined to be defective in the defect existence determining step; and a display step for displaying positions of the detected defective sections on the specimen surface, and the defect sizes obtained in the defect size determining step.

A third aspect of the present invention includes: illumination light regulating means for regulating illumination light that has been emitted from a light source to a beam of light having a desired quantity of light, position, beam diameter, and polarization state; illumination intensity distribution control means for guiding the beam obtained by the illumination light regulating means to a specimen surface at a desired angle of incidence, and for controlling an illumination intensity distribution so that the illumination intensity distribution of light illuminating the surface of the specimen is substantially uniform in a certain direction on the specimen surface; specimen scanning means for, at a position on the specimen surface where the illumination intensity distribution control means irradiates the specimen with the illumination light, moving the specimen in a direction substantially perpendicular to the direction in which the illumination intensity distribution will be substantially uniform; scattered-light detection means for detecting, of scattered light emitted from the specimen surface by the illumination of the illumination light having the controlled illumination intensity distribution, a plurality of scattered-light components emitted in a plurality of directions different from each other, and for outputting a plurality of corresponding scattered-light detection signals corresponding to the detected scattered-light components; defect determining means for determining existence of defects by processing at least one of the scattered-light detection signals obtained in the scattered-light detection means; defect size determining means for determining sizes of the defects by processing at least one of the scattered-light detection signals corresponding to the sections determined to be defective in the defect existence determining means; and display means for displaying positions of the detected defective sections on the specimen surface, and the defect sizes obtained in the defect size determining means.

Advantageous Effects of Invention

The present invention scans the entire surface of a specimen within a short time, detects microscopic defects on the surface while reducing thermal damage to the specimen, calculates sizes of the detected defects accurately, and outputs stable inspection results.

These and other objects, features and advantages of the invention will be apparent from the following more particular description of preferred embodiments of the invention, as illustrated in the accompanying drawings.

BRIEF DESCRIPTION OF DRAWINGS

FIG. 16 is a schematic showing a first example of means used to reduce energy per pulse by means of optical path branching and combining in the illumination unit according to the present invention;

FIG. 17 shows energy-per-pulse reduction results based on optical path branching and combining;

DESCRIPTION OF EMBODIMENTS

Figure 1:
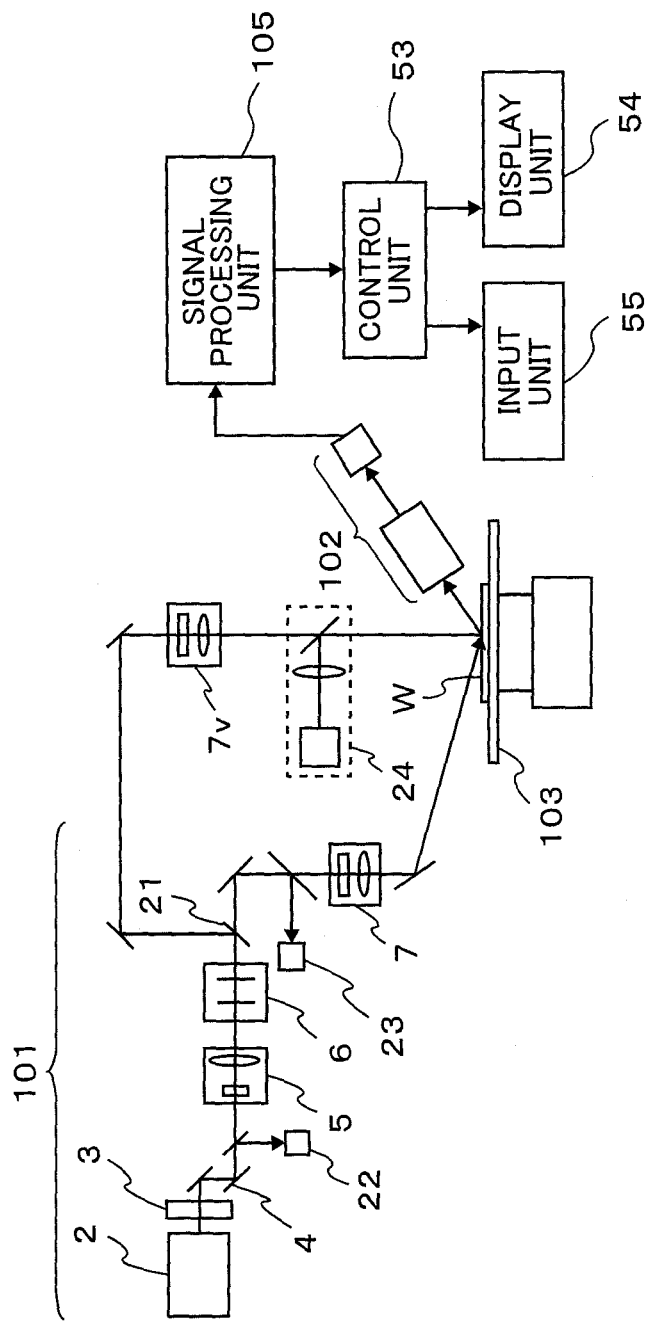
FIG. 1 is an overall schematic block diagram showing an embodiment of a defect inspection device according to the present invention.

A schematic exemplary configuration of a defect inspection device according to an embodiment of the present invention is described below referring FIG. 1. The defect inspection device includes an illumination unit 101, a detection unit 102, a stage 103 on which a specimen W can be mounted, a signal processing unit 105, a control unit 53, a display unit 54, and an input unit 55, as appropriate. The illumination unit 101 includes a laser light source 2, an attenuator 3, an exit beam regulator 4, a beam expander 5, a polarization controller 6, and an illumination intensity distribution controller 7, as appropriate. A laser light beam that has been emitted from the laser light source 2 is controlled to desired beam intensity by the attenuator 3, adjusted to a desired beam position and a beam traveling direction by the exit beam regulator 4, and is controlled to a desired beam diameter by the beam expander 5. The beam is next controlled to a desired polarization state by the polarization controller 6, then controlled to a desired intensity distribution by the illumination intensity distribution controller 7, and then illuminated at a target region of the wafer W.

An angle of incidence of the illumination light with respect to the specimen surface is determined by a position and angle of a reflecting mirror of the exit beam regulator 4, disposed in an optical path of the illumination unit 101. The incident angle of the illumination light is set to an angle appropriate for detecting microscopic defects. As the incident angle of the illumination light increases, that is, an illumination elevation (an angle between the specimen surface and an illumination optical axis) decreases, the scattered light from microscopic irregularities on the specimen surface which acts as noise for the scattered light from microscopic contamination on the specimen surface (haze) becomes weaker. Thus, small incident angles of the illumination light are suitable for detecting microscopic defects. Accordingly, if the scattered light from the microscopic irregularities on the specimen surface obstructs the detection of microscopic defects, the incident angle of the illumination light is preferably set to 75 degrees or larger (the elevation is preferably 15 degrees or smaller). On the other hand, in off-axis illumination, as an incident angle of the illumination light is smaller, an absolute quantity of the scattered light from microscopic contamination gets greater. Therefore if a shortage of the amount of scattered light scattered from a defect obstructs the detection of the defect, the incident angle of the illumination light is preferably set to 60 to 75 degrees (the elevation preferably is between 15 and 30 degrees). In addition, in off-axis illumination, the polarization controller 6 of the illumination unit 101 makes the illumination light P-polarized. This increases the amount of light scattered from the defect on the specimen surface in comparison with the amount of light with different polarization.

In addition, as shown in FIG. 1, the mirror 21 and other appropriate mirrors are disposed in the optical path of the illumination unit 101 as required. The optical path of the illumination light changes so that the light is irradiated from a direction substantially perpendicular to the specimen surface (vertical illumination). During the irradiation, the illumination intensity distribution on the specimen surface is controlled by an illumination intensity distribution controller 7v, as with the case of off-axis illumination. When a beam splitter is inserted at the same position as that of the mirror 21 to obtain scattered light from off-axis illumination light and a concaved defect on the specimen (polishing scratches or crystalline defects in a crystal material), vertical illumination in which light enters the specimen surface at a substantially vertical angle is suitable. An illumination intensity distribution monitor 24 shown in FIG. 1 is described in detail later.

For the detection of microscopic defects near the specimen surface, the laser light source 2 is such that has high power of 2 W or more and oscillates ultraviolet or vacuum-ultraviolet laser beams of a short wavelength (355 nm or less) to minimize penetration into the specimen. The diameter of an exit beam is about 1 mm. For the detection of defects inside the specimen, the laser light source 2 is such that oscillates visible or infrared laser beams of a wavelength at which the light relatively easily penetrates into the specimen.

The attenuator 3 includes a first polarizer, a half-wave plate rotatable around the optical axis of the illumination light, and a second polarizer, as appropriate. Light that has entered the attenuator 3 is converted into a linearly polarized light by the first polarizer, next is turned to an optional polarization direction according to a slow-axis azimuth of the half-wave plate, and then passes through the second polarizer. The intensity of the light is reduced at an optional ratio by controlling the azimuth of the half-wave plate. The first polarizer is not needed if the light entering the attenuator 3 has a sufficiently high degree of linear polarization. The attenuator 3 is to have been calibrated the relationship between an input signal level and a light reduction rate beforehand. The attenuator 3 may be an ND filter having a gradation density distribution.

The exit beam regulator 4 includes plural reflecting mirrors. While the regulator 4 in the present example includes two reflecting mirrors, the number of reflecting mirrors is not limited and the regulator 4 may have three or more reflecting mirrors when needed. Here, an imaginary three-dimensional rectangular coordinate system (XYZ coordinates) is defined, and the light incident upon the reflecting mirrors is assumed to travel in a +X direction. A first reflecting mirror is set to deflect the incident light in a +Y direction (incidence/reflection in an XY plane), and a second reflecting mirror is set to deflect the incident light that has been reflected by the first reflecting mirror in a +Z direction (incidence/reflection in a YZ plane). At these reflecting mirrors, the position and traveling direction (angle) of the light emitted from the exit beam regulator 4 are controlled by parallel movement and tilt angle adjustment. The incident/reflection plane (XY plane) of the first reflecting mirror and the incident/reflection plane (YZ plane) of the second reflecting mirror are disposed so as to cross at right angles as described above. Therefore, positions and angles of the light emitted from the exit beam regulator 4 (travels in a +Z direction) in XZ-plane and in YZ-plane can be controlled independently.

The beam expander 5 includes at least two lens groups and has a function that enlarges a diameter of incoming parallel beams of light. The beam expander 5 may be of a Galilean type including a combination of a concave lens and a convex lens for example. The beam expander 5 is placed on a translation stage which is movable along two or more axes and its position can be adjusted to align a predetermined beam position and the center of the expander. A tilt angle adjusting function for adjusting the angle of the entire beam expander 5 is also included to align an optical axis of the beam expander 5 with a predetermined beam optical axis. The enlargement ratio of the beam diameter can be controlled by adjusting the interval between the lenses (zoom mechanism). If the beams entering the beam expander 5 are not parallel, the enlargement in diameter and collimation (quasi-parallelization) of the beams are conducted at the same time during the adjustment of the lens interval. The collimation of the beams may be conducted by providing a collimating lens independent of the beam expander 5 upstream of the expander. The enlargement rate for the beam diameter of the beam expander 5 is about 5 to 10 times: for example, a beam emitted from the light source of a diameter about 1 mm would be enlarged to about 5 to 10 mm.

The polarization controller 6 includes a half-wave plate and a quarter-wave plate, and controls the illumination light to any polarization state. Monitors 22 and 23 measures, in a midway of the optical path of the illumination unit 101, data on the state of the light incident upon the beam expander 5 and the state of the light incident upon the illumination intensity distribution controller 7.

Figure 2:
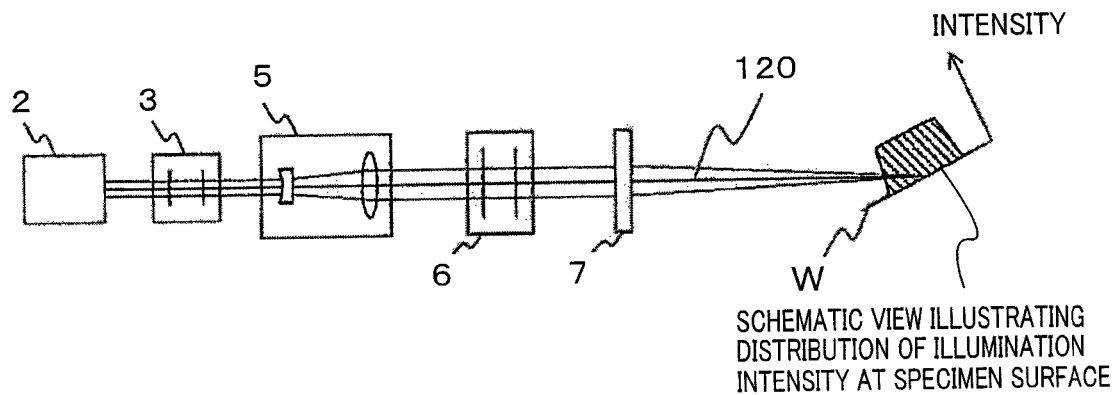
FIG. 2 is a schematic showing a first example of an illumination intensity distribution shape implemented by an illumination unit according to the present invention.
Figure 3:
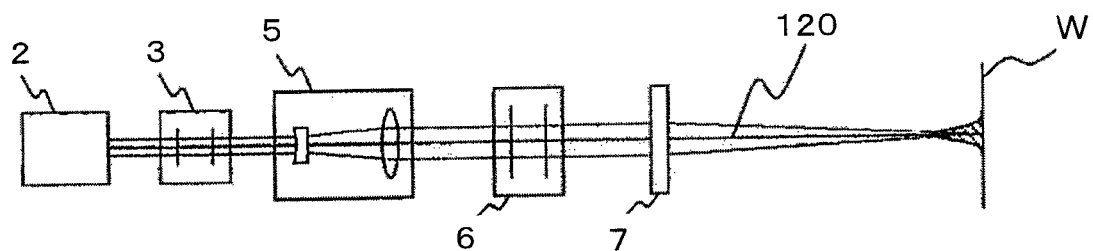
FIG. 3 is a schematic showing a second example of an illumination intensity distribution shape implemented by the illumination unit according to the present invention.

FIGS. 2 to 6 show schematic diagrams of relationships in position between the optical axis 120 and an intensity distribution shape of the illumination light guided to the specimen surface by the illumination unit 101. Constituent elements of the illumination unit 101 shown in FIGS. 2 to 6 are part of the illumination unit configuration, and the exit beam regulator 4, the mirror 21, the beam monitors 22, 23, and other elements are omitted from the figures. A schematic cross-sectional view of an incidence plane of off-axis illumination light (the plane including the illumination optical axis and a specimen surface normal) is shown in FIG. 2. The off-axis illumination light is inclined to the specimen surface in the incident plane. The illumination unit 101 forms a substantially uniform illumination intensity distribution in the incidence plane. Length of a portion uniform in illumination intensity is about 100 µm to 1 mm so as to inspect a wide area within a unit time. A schematic cross-sectional view of the plane which includes the specimen surface normal and is perpendicular to the incident plane of off-axis illumination is shown in FIG. 3. In this plane, the illumination intensity distribution on the specimen surface is such that a peripheral area has a weak intensity relative to that of the central area. More specifically, this illumination intensity distribution is a gaussian distribution that reflects the intensity distribution of the light entering the illumination intensity distribution controller 7, or an intensity distribution that resembles a first kind/first-order Bessel function or a sinc function that reflects an aperture shape of the illumination intensity distribution controller 7. Length of the illumination intensity distribution in the incident plane (length of a region having at least 13.5% of maximum illumination intensity) ranges between about 5 µm and 20 µm. This is smaller than the length of the above portion uniform in illumination intensity in the incident plane so as to reduce haze arising from the specimen surface. The illumination intensity distribution controller 7 includes optical elements such as a non-spherical lens, diffractive optical element, cylindrical lens array, and light pipe, which are described later. The optical elements constituting the illumination intensity distribution controller 7 are placed perpendicularly to the illumination optical axis, as shown in FIGS. 2, 3.

Figure 7:
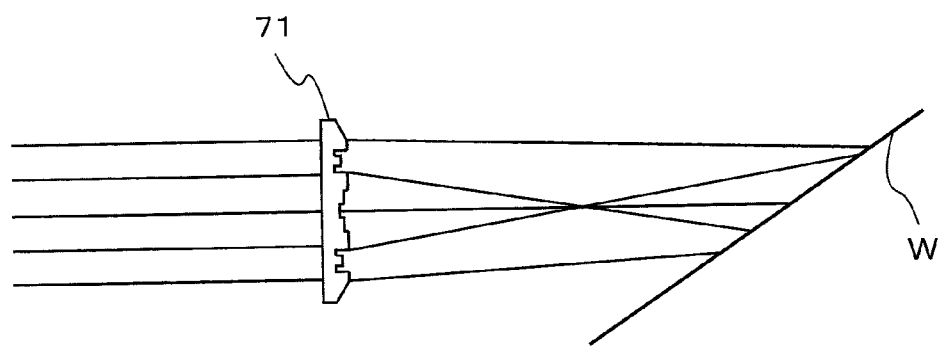
FIG. 7 is a schematic showing a first example of an optical element included in an illumination intensity distribution controller according to the present invention.

The illumination intensity distribution controller 7 includes an optical element that acts upon the intensity distribution and a phase distribution of the light entering the controller 7. One of such optical elements constituting the illumination intensity distribution controller 7 is a diffractive optical element (DOE) 71 shown in FIG. 7. The diffractive optical element 71 is of a substrate that is made from a material which transmits the incident light and whose surface is corrugated with micro patterns of a size equivalent to or smaller than a wavelength of light. As the material that transmits incident light, fused quartz is used for ultraviolet light. The diffractive optical element 71 is preferably coated with an anti-reflection film to suppress attenuation of the light passing through the diffractive optical element 71. Lithography is used to form the micro corrugation. The light that has passed through the beam expander 5 and has been quasi-paralleled is further passed through the diffractive optical element 71, thereby forming an illumination intensity distribution corresponding to the corrugation of the diffractive optical element 71 on the specimen surface. The corrugated surface shape of the diffractive optical element 71 is designed and formed based on calculations using Fourier optics theory, so that the illumination intensity distribution formed on the specimen surface will be a long uniform distribution in the incident plane. The optical element of the illumination intensity distribution controller 7 includes a translational control mechanism and a rotational control mechanism both having two or more axes. These mechanisms enable the position and the angle of the element with respect to the optical axis of the incident light to be adjustable. A focus adjustment mechanism for adjusting focus by moving the element in the optical axis direction is also provided.

Figure 14:
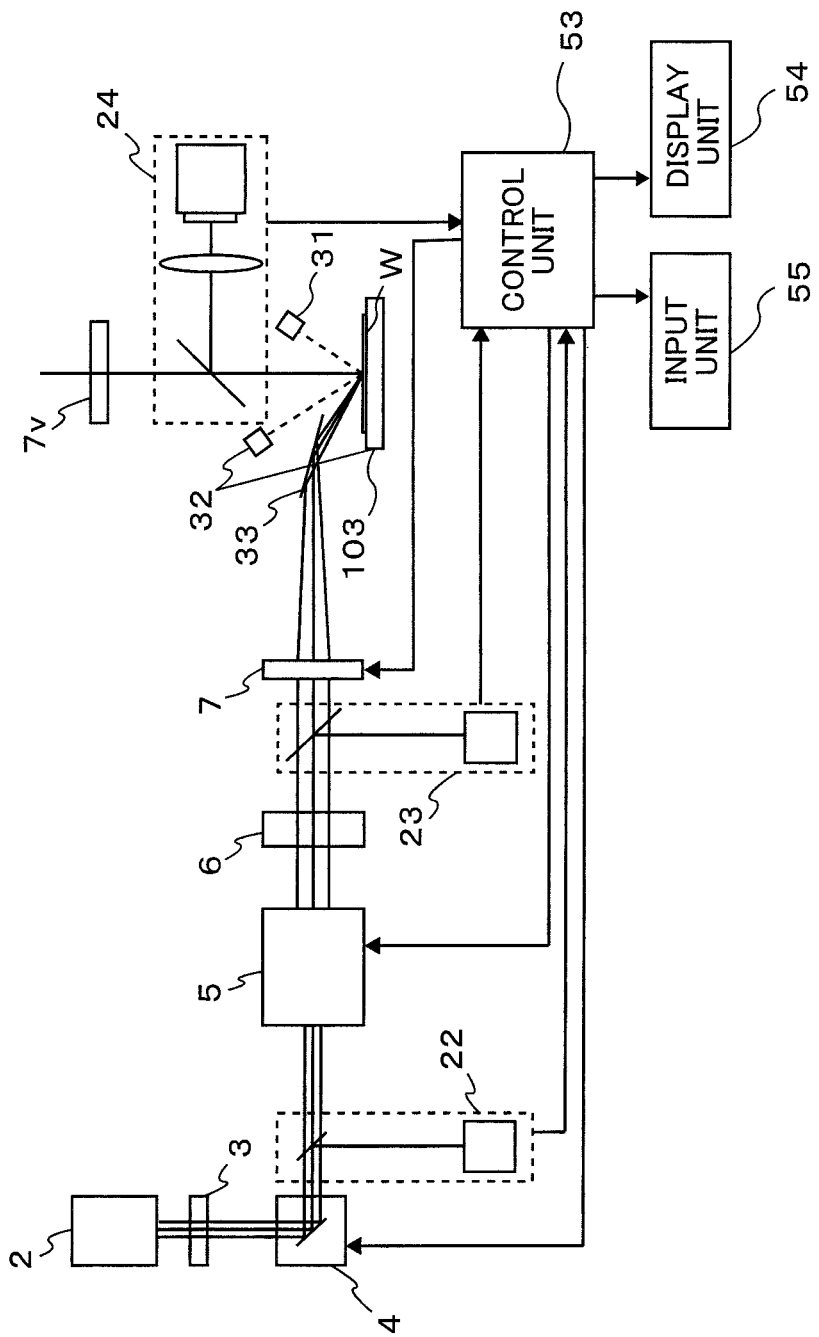
FIG. 14 is a schematic showing a first example of means used to measure and control data relating to a state of illumination light in the illumination unit according to the present invention.

The illumination light state-measuring means in the illumination unit 101 is described below using FIG. 14. The beam monitor 22 measures and outputs data corresponding to the position and angle (traveling direction) of the illumination light which has passed through the exit beam regulator 4. The beam monitor 23 measures and outputs data corresponding to the position and wavefront of the illumination light entering the illumination intensity distribution controller 7.

The position measurement of the illumination light at the beam monitor 22 is conducted by measuring the center of gravity of the illumination light intensity. Specifically, a position-sensitive detector (PSD) or an image sensor such as a CCD sensor or CMOS sensor is among the position-measuring means. The angle measurement of the illumination light is conducted by the beam monitor 22 by using a beam position sensor or an image sensor placed at a position more remote from the light source than the above position-measuring means. The position and angle of the illumination light measured by the beam monitor 22 are input to the control unit 53 and then displayed on the display unit 54. When the position or angle of the illumination light deviates from a predetermined position or angle, the exit beam regulator 4 controls the light back to the predetermined position or angle.

Figure 15:
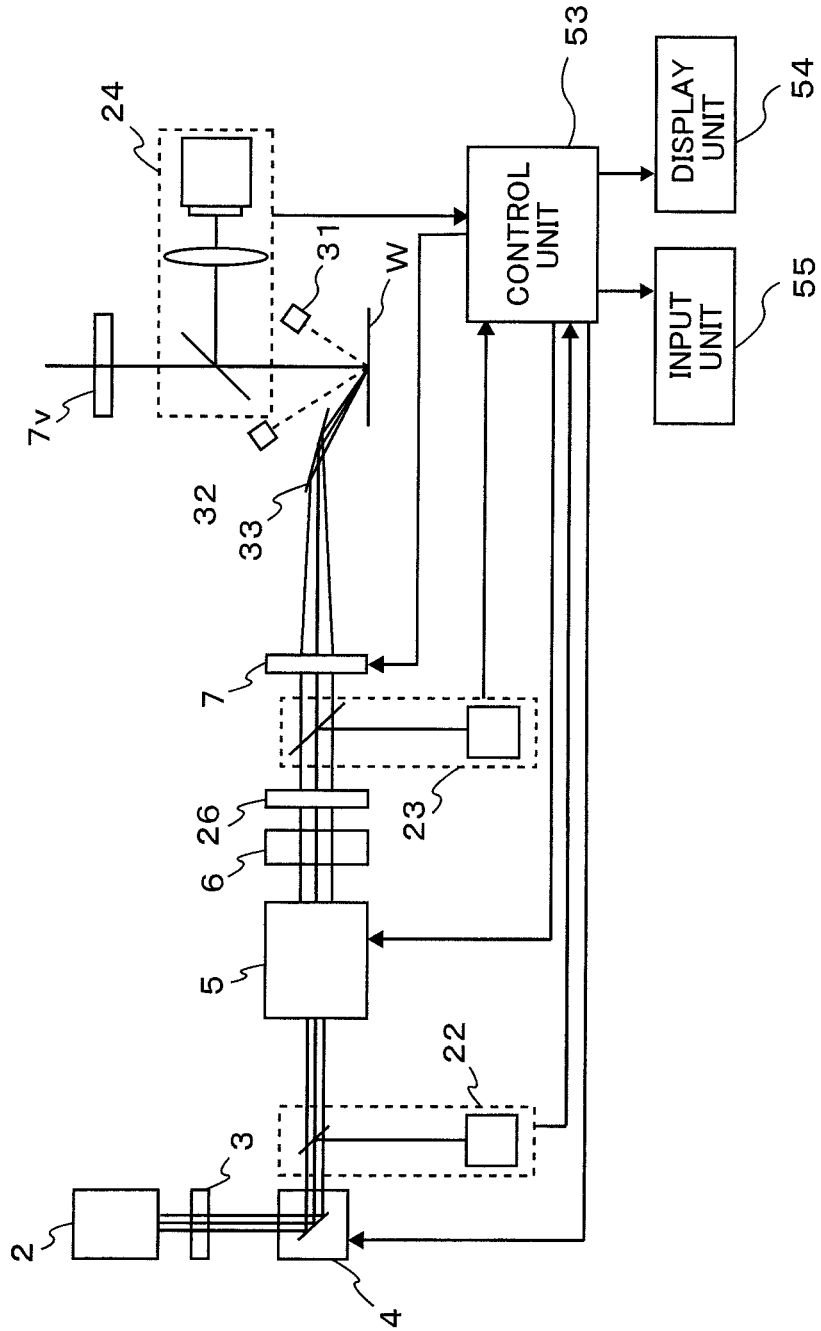
FIG. 15 is a schematic showing a second example of means used to measure and control the data relating to a state of illumination light in the illumination unit according to the present invention.

Position measurement of the illumination light by the beam monitor 23 is conducted by means substantially same with the position-measuring means of the beam monitor 22. However, since the beam diameter is expanded to several millimeters or more at the measurement position of the beam monitor 23, the measurement position is projected in reduced size on a light-receiving surface of a detection element of the position-measuring means (a position-sensitive detector for instance), prior to the measurement. Wavefront measurement of the illumination light by the beam monitor 23 is conducted to measure a parallelism level of the light entering the illumination intensity distribution controller 7. The illumination light is measured with a shearing interferometer or a Shack-Hartmann wavefront sensor. A shearing interferometer is such that has an optical glass plate with both sides planarly polished and thickness of about several millimeters, and the optical glass is inserted in the illumination optical path obliquely inclined. Light reflected from an upper surface and a lower surface is projected on a screen and the pattern of interference fringes is observed to thereby measure a divergence/convergence state of the illumination light. The SPU-25, manufactured by Sigma Koki Co., Ltd., can be named as an example of shearing interferometers. The illumination light divergent/convergent state can be automatically measured by disposing a CCD sensor or an image sensor such as a CMOS sensor at a screen position. A Shack-Hartmann wavefront sensor employs a micro lens array to divide a wavefront, projects the divided wavefronts on an image sensor such as a CCD sensor, and measures inclinations of each wavefront from variations in the projection position. Compared with shearing interferometers, Shack-Hartmann wavefront sensors can conduct detailed wavefront measurements: for example, can measure partial disturbances in wavefront. When the light entering the illumination intensity distribution controller 7 is found through wavefront measurement to be not quasi-parallel light and diverged or converged, the illumination light can be neared to quasi-paralleled light by moving the lenses of the beam expander 5, in the preceding stage of the controller 7, along the optical axis. When, through the wavefront measurement, the light entering the illumination intensity distribution controller 7 is found to be partially inclined, the wavefront can be brought more planar, in other words, the illumination light can be neared to quasi-paralleled light in the following way. As shown in FIG. 15, a spatial light phase modulator 26 is inserted into the preceding stage of the illumination intensity distribution controller 7, and an appropriate phase difference is imparted to each position of a cross-section of the light beam so that the wavefront will be more planar. The above wavefront accuracy measuring/controlling means suppresses wavefront accuracy of the light (a departure from a predetermined wavefront (design value)) entering the illumination intensity distribution controller 7 to $\lambda/10$ rms or less.

The illumination intensity distribution on the specimen surface conditioned by the illumination intensity distribution controller 7 is measured by the illumination intensity distribution monitor 24. When vertical illumination is employed, as shown in FIG. 1, the illumination intensity distribution on the specimen surface conditioned by the illumination intensity distribution controller 7v is measured by the illumination intensity distribution monitor 24 as well. The illumination intensity distribution monitor 24 detects the specimen surface as an image by imaging the surface on an image sensor such as a CCD sensor or a CMOS sensor via lenses. The image of the illumination intensity distribution that is detected by the illumination intensity distribution monitor 24 is processed by the control unit 53 to calculate factors such as the center of gravity of intensity, maximum intensity, maximum intensity position, width and length of the illumination intensity distribution (i.e., width and length of the illumination intensity distribution region of which intensity is equal to or larger than a predetermined intensity level or of which intensity ratio is equal to or larger than a predetermined ratio with respect to the maximum intensity level). Calculation results are displayed at the display unit 54 along with a profile shape, a cross-sectional waveform, etc. of the illumination intensity distribution.

In off-axis illumination, a change in height of the specimen surface changes the position of the illumination intensity distribution and causes defocusing to disturb the illumination intensity distribution. In order to suppress disturbing the illumination intensity distribution, the height of the specimen surface is measured and if the height is shifted, the deviation is corrected by the illumination intensity distribution controller 7 or by Z-axial height adjustment of the stage 103. The height measurement of the specimen surface is conducted using a beam emitter 31 and a beam receiver 32 that receives the beam emitted from the beam emitter 31 and reflected from the specimen surface. The beam emitter 31 includes a light source such as a semiconductor laser, and a projection lens. The beam receiver 32 includes a light receiving lens and a position-sensitive detector. For measuring the height of a shiny specimen surface such as a semiconductor silicon surface or magnetic disk substrate surface, the beam emitter 31 and the beam receiver 32 are arranged so that the light emitted from the beam emitter 31 and specularly reflected from the specimen surface will be detected at the beam receiver 32. The change in the height of the specimen surface is detected, in accordance with the principles of triangulation, as a position deviation of the beam spot detected by a position-sensitive detector in the beam receiver 32.

A position deviation of illumination light irradiation towards an internal direction of the specimen surface, due to a change in height of the specimen surface, is corrected by adjusting a deflection angle with deflection means 33. Deflection means 33 is placed downstream of the illumination intensity distribution controller 7 and directs the illumination light towards the specimen surface. The deflection means 33 includes a reflecting mirror for deflecting the illumination light, and a piezoelectric element for adjusting a tilt angle of the reflecting mirror with respect the optical axis of the light. The deflection means 33 adjusts the tilt angle in a range of about ±1 mrad at a frequency of at least 400 Hz. The deviation in illumination light irradiating position towards the internal direction in the specimen surface can be calculated from the measured height change and the incident angle of the illumination light. In order to correct the deviation, the deflection means 33 receives a control signal output from the control unit 53 and accommodates the reflecting mirror. The deviation in illumination light irradiating position towards the internal direction in the specimen surface can also be found by directly measuring the center of gravity and/or other factors of the illumination intensity distribution using the illumination intensity distribution monitor 24. When the deviation in illumination light irradiating position towards the internal direction of the specimen surface is corrected by the deflection means 33, length of the optical path between the illumination intensity distribution controller 7 and the specimen surface changes from the value before correction. Depending on the degree of the change, defocusing of the illumination spot may occur. The change in the length of the optical path can be calculated from the measured height variation and the incident angle of the illumination light, and defocusing is reduced on the basis of the thus-calculated value. The reduction of defocusing takes place by adjusting the position of the optical element of the illumination intensity distribution controller 7, in the direction of the optical axis, or by adjusting the divergence angle of the beam expander 5.

Figure 32:
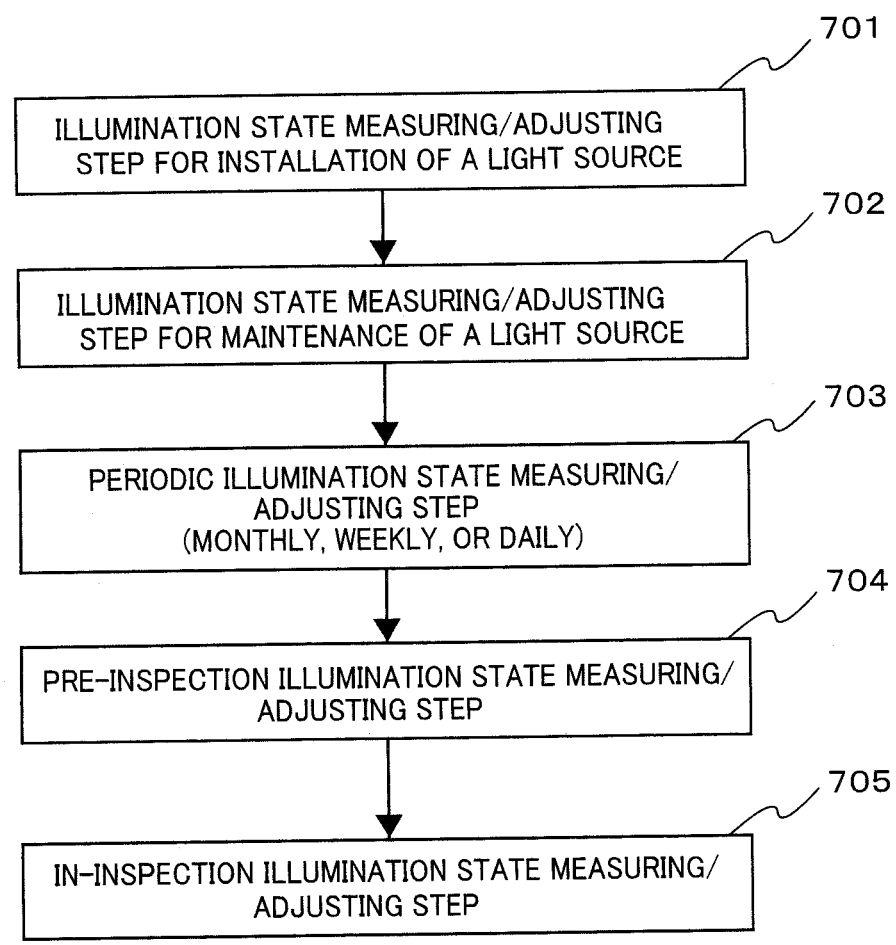
FIG. 32 is a flow diagram of illumination state control in an illumination unit according to the present invention.

Time intervals and timing at which each constituent element of the illumination unit 101 controls an illumination state of illumination light are described below using FIG. 32. When installing a light source, an illumination state measuring/controlling step 701 such that controls the elements stepwise from the upstream of the optical path of the illumination unit 101, from the attenuator 3, the exit beam regulator 4, the beam expander 5, the polarization controller 6, the illumination intensity distribution controller 7, to the deflection means 33, is implemented. In the installing, the illumination light is controlled to travel along a designed optical path and pass through the illumination intensity distribution controller 7 with a predetermined amount of light, beam diameter, divergence angle, wavefront accuracy, and polarization state. The illumination state measuring/controlling step 701 for installation of a light source includes the case where the light source 2 is replaced by a new one with equivalent functionality and performance, according to a change in the state concerning the life of the light source such as a decrease in output power due to long time operation A high-power laser light source used as the light source 2 degrades over time. That is, the light irradiating position relative to the non-linear optical crystal within the light source degrades with long term usage. The light irradiating position relative to the non-linear optical crystal is therefore shifted periodically (that is, the position of the crystal relative to the optical path is shifted) for extended longevity. After the shifting, the optical path of the light emitted from the laser light source may not be reproduced and the passing position or traveling direction of the light may be deviated. In order to measure, correct the deviation and put back illumination to its original state, illumination state measuring/controlling step 702 for maintenance of a light source takes place. In the illumination state measuring/controlling step 702 for maintenance of a light source, the light emitted from the light source 2 located most upstream of the illumination unit 101 may deviate in position, emitting direction, divergence angle, and polarization state. The state of illumination light is therefore measured by all of the illumination state measuring elements: beam monitors 22, 23 and illumination intensity distribution monitor 24. Any of the attenuator 3, the exit beam regulator 5, the beam expander 5, the polarization controller 6, the illumination intensity distribution controller 7, or the deflection means 33 is adjusted as required. The illumination state measuring/controlling step 702 for maintenance of a light source is performed at a timing such as after shifting the light irradiating position relative to the non-linear optical crystal within the light source, or after cleaning the optical element within the light source for the maintenance of the light source, or, when a high-power lamp light source or a lamp-excited laser light source is used as the light source 2, after replacing the lamp. The step 702 is performed at time intervals of several months or several hundred hours.

An illumination state may also vary due to changes in the output of the light source 2 over time or changes in location or location angle of the optical elements constituting the illumination unit 101 for drift. In order to control this, a periodic illumination state measuring/adjusting step 703 takes place monthly, weekly, or daily. The parameters relating to illumination states are measured by all of the illumination state measuring elements; namely the beam monitors 22, 23 and the illumination intensity distribution monitor 24, and either of the attenuator 3, the exit beam regulator 4, the beam expander 5, the polarization controller 6, the illumination intensity distribution controller 7, or the deflection means 33 is adjusted as required.

After the control in periodic illumination state measuring/adjusting step 703, changes in an environment of the illumination unit 101 (atmospheric pressure, temperature, etc.) or changes in the position and the angle of the optical elements due to drift may occur. Pre-inspection illumination state measuring/adjusting step 704 takes place to correct these changes. Pre-inspection illumination state measuring/adjusting step 704 is executed more frequently than the periodic illumination state measuring/adjusting step 703. If the operation time of step 704 is too long, time efficiency decreases and an actual operation time of the inspection device is reduced. Therefore, the illumination state measuring/adjusting step 704 can be executed within a short time. Specifically, the illumination intensity distribution on the specimen surface which is the final output data from the illumination unit 101 is measured by the illumination intensity distribution monitor 24. Adjustment of specimen surface height with the stage 103, adjustment of the illumination light irradiating position by the deflection means 33, or adjustment of the position of the optical elements in the illumination intensity distribution controller 7 is executed accordingly.

In-inspection illumination state measuring/adjusting step 705 takes place to suppress changes in illumination intensity distribution due to shifts in the height of the specimen surface by using optical, mechanical means at the illumination unit 101 or the stage 103. Step 705 may also correct impacts caused by these changes at the detection unit 102 and signal processing unit 105 present at the following stage. Suppression of the changes in illumination intensity distribution due to shifts in the height of the specimen surface, with optical, mechanical means, is performed as mentioned in the description of the illumination intensity distribution monitor 24. That is, a change of the center of gravity in the illumination intensity distribution or a change in the shape of the distribution due to defocusing is corrected, according to the results measured by the illumination intensity distribution monitor 24 or the specimen surface height measuring means. The correction is conducted by adjusting the deflection means 33, the illumination intensity distribution controller 7, the spatial light phase modulator 26, or the stage 103. Further, the correction is conducted in real time during the inspection of the specimen surface. The impact affected on the inspection result by the changes in illumination intensity distribution due to shifts in the height of the specimen surface refers to the following. That is, when the illumination intensity distribution is not completely flat, illumination intensity differs depending on positions of a defect where light transmit so that an amount of scattered light varies significantly. Dimensions of the defect or detection sensitivity of the defect which is calculated from the amount of scattered light by the signal processing unit 105 in the following stage (described later) becomes variable as well. To suppress such variability, values of the signal strength distribution measured by the illumination intensity distribution monitor 24 are recorded for each scanning position during inspection. The recorded values are applied in the signal processing unit 105 to correct a threshold level used for defect detection or a defect signal value used for defect size calculation.

In-inspection illumination state measuring/adjusting step 705 takes place to suppress changes in illumination intensity distribution due to shifts in the height of the specimen surface by using optical or mechanical means at the illumination unit 101 or the stage 103. Step 705 may also correct impacts caused by these changes at the detection unit 102 and signal processing unit 105 present at the following stage. Controlling the changes in illumination intensity distribution due to shifts in the height of the specimen surface, with optical, mechanical means, is performed as mentioned in the description of the illumination intensity distribution monitor 24. That is, a change of the center of gravity in the illumination intensity distribution or a change in the shape of the distribution due to defocusing is corrected, according to the results measured by the illumination intensity distribution monitor 24 or the specimen surface height measuring means. The correction is conducted by adjusting the deflection means 33, the illumination intensity distribution controller 7, the spatial light phase modulator 26, or the stage 103. Further, the correction is conducted in real time during the inspection of the specimen surface.

When a pulse laser which has high output power is used as the light source 2, the energy of illumination given to the specimen concentrates at the moment a pulse enters. This instant temperature rise associated with the entry of the pulse may thermally damage the specimen. As a way to avoid this, the optical path of the pulsed laser is branched to have an optical path difference and then combined. Energy per pulse can be effectively reduced while maintaining total energy as shown in FIG. 17.

An example of an optical system for implementing the above is shown in FIG. 16. Illumination light passed through the beam expander 5 enters a polarizing beam splitter 151. The optical path of the light branches into a first optical path of the light reflected at the polarizing beam splitter 151 and a second optical path of the light that transmitted through the polarizing beam splitter 151. The first optical path is reflected backward by a retroreflector 152 and then reflected by a polarizing beam splitter 153 to be combined with the second optical path. The retro reflector 152 includes at least two reflecting mirrors perpendicular to each other, and the retroreflector 152 reflects the input light 180-degree opposite direction. As to equalize the light intensity of the light reflected at the polarizing beam splitter 151 and the light passed through the polarizing beam splitter 151, a wave plate 150 adjusts the illumination light into a circular polarized light or a 45-degree linear polarized light, etc. If differential length between the first and second optical paths is expressed as L, a time interval (Δtp) between the passage of the pulse through the first optical path and that of the pulse through the second optical path is expressed as Δtp=L/c. When the time interval Δtp is equal to or longer than the time needed to alleviate a temperature rise due to entry of one pulse, a instant increase in temperature of the specimen due to one pulse and an increase in temperature of the specimen for accumulation of heat due to a plurality of pulses can be controlled.

In the combining process of the optical path, if combining accuracy is low, the two paths combined may deviate from each other in position or traveling direction. In such case, the illumination light entering the illumination intensity distribution controller 7 departs from an ideal state (in the present embodiment, quasi-parallel gaussian beam). Accordingly, the illumination intensity distribution finally formed on the specimen surface deviates from a desired state. This problem is more likely to occur when the optical path difference between the two optical paths is made greater so as to obtain a sufficient time interval Δtp of pulses. The smaller a diameter of the beam, more significant the impact on the deviation in position between the beams of the two optical paths becomes (the deviation from the gaussian beam of the combined-light intensity distribution is significant). In the present embodiment, therefore, an optical path is branched and combined at the stage succeeding the beam expander 5 after beam diameter expansion, thereby reducing the impact of the deviation in position of the two optical paths. The first optical path may be reflected by using two independent mirrors instead of the retroreflector 152. However in this case, a relative angle deviation between the two mirrors may cause an angle deviation between the two beams combined. Thus the present embodiment uses the retroreflector 152 so this problem does not occur. In addition, while the illumination unit 101 including the optical system shown in FIG. 16 is set up on an optical surface table formed of aluminum or the like, the optical surface table may be distorted due to changes in temperature or other environmental parameters. This may shift the position of the retroreflector 152 in an X-direction of FIG. 16. The position of the beam reflected from the retroreflector 152 and returned to the polarizing beam splitter 153 may accordingly shift in the X-direction. For these reasons, the polarizing beam splitters 151, 153 and the retroreflector 152 are provided on a surface table 154 which is mounted on the optical surface table supporting the illumination unit 101. These optical elements can thus maintain relative position relationship without being affected by matters such as distortion due to the layout or shape of the entire optical surface table supporting the illumination unit 101. In addition, the surface table 154 may be formed of a low-expansion rate material such as a glass ceramic to effectively suppress distortion due to changes in temperature. Employing the low-expansion rate material only to form the surface table 154 has an advantage in cost, over using such a material to construct the entire optical surface table supporting the illumination unit 101.

Figure 19:
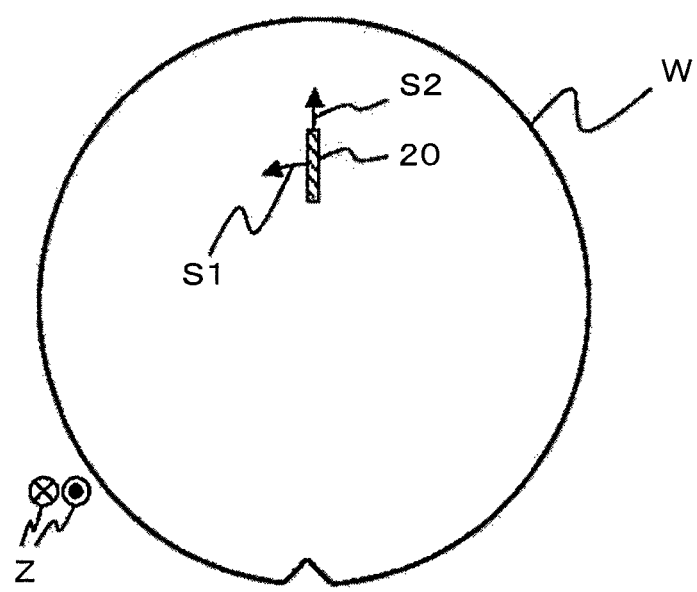
FIG. 19 is a schematic illustration of a scanning direction and an illumination distribution shape on a specimen surface.

The illumination intensity distribution shape (illumination spot 20) formed on the specimen surface by the illumination unit 101, and a method of scanning the specimen are described below referring to FIGS. 19 and 20. A circular semiconductor wafer is presumed as the specimen W. The stage 103 includes a translational stage, a rotational stage, and a Z-stage for adjusting specimen surface height (neither is shown in the figures). As mentioned, the illumination spot 20 has an illumination intensity distribution elongated in one direction. Let this direction be S2, and let a direction substantially perpendicular to S2 be S1. The rotational stage is rotated to scan the specimen in the circumferential direction S1 of a circle whose center is the rotational axis of the rotational stage. The translational stage is translated to scan in the translational direction S2 of the translational stage. While the specimen is scanned in the scanning direction S1 through one full rotation, the specimen is scanned in the scanning direction S2 through a distance equal to or less than a longitudinal dimension (length) of the illumination spot 20. The illumination spot 20 thereby follows a helical path T on the surface of the specimen W and the entire surface of the specimen 1 can be scanned.

Estimation of the illumination power without causing thermal damage to the specimen is described below. According to the "Handbook of Laser Process Technology" (published in 1992 by Asakura Publishing Co., Ltd.), when a light having a rectangularly uniform illumination intensity distribution is irradiated on the semi-infinite surface, a temperature rise at a position (x, y, z) is represented as the following.

$$T(x, y, z, t) = \frac{\epsilon P \sqrt{\kappa}}{16\sqrt{\pi abK}} \int_0^t \frac{1}{\sqrt{\tau}} \left( \text{erf} \frac{x+a}{2\sqrt{\kappa\tau}} - \text{erf} \frac{x-a}{2\sqrt{\kappa\tau}} \right) \times \left( \text{erf} \frac{y+b}{2\sqrt{\kappa\tau}} - \text{erf} \frac{y-b}{2\sqrt{\kappa\tau}} \right) \exp\left(-\frac{z^2}{4\kappa\tau}\right) d\tau \quad \text{expression 1}$$

Here, $\epsilon$ is an absorption coefficient of the illumination light on the surface, P is the laser power, $\kappa$ is thermal diffusivity, K is thermal conductivity, "a" and "b" are halves of width and length of the illumination, and "erf" is an error function. Also, "x", "y", "z" are coordinates with a central portion of the rectangular illumination distribution as an origin, and "z" corresponds to a depth or perpendicular direction of the semi-infinite surface. The thermal diffusivity $\kappa$ is derived from the relationship between thermal conductivity K, density $\rho$, and specific-heat capacity "c"; expressed as $\kappa = K/(\rho c)$. According to expression 1, the temperature rise at the center of the rectangular illumination distribution is represented as below.

$$T(0, 0, 0, t) = \frac{\epsilon P \sqrt{\kappa}}{4\sqrt{\pi abK}} \int_0^t \frac{1}{\sqrt{\tau}} \text{erf} \frac{a}{2\sqrt{\kappa\tau}} \text{erf} \frac{b}{2\sqrt{\kappa\tau}} d\tau \quad \text{expression 2}$$

In addition, a steady-state value of the temperature rise where irradiation was implemented for an extended time of is represented as below:

$$T(0, 0, 0, \infty) = \frac{\epsilon P}{2\pi abK} \left( a \sinh^{-1} \frac{b}{a} + b \sinh^{-1} \frac{a}{b} \right) \quad \text{expression 3}$$

Figure 20:
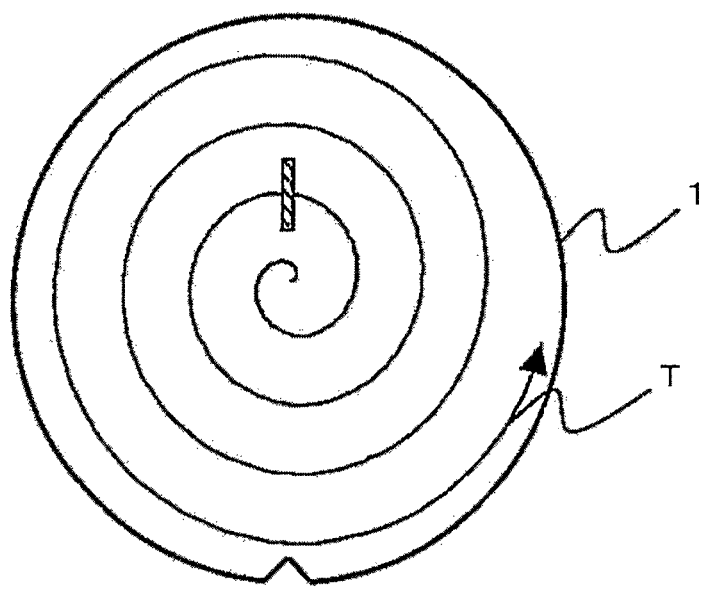
FIG. 20 is a schematic illustration showing a path of an illumination spot during scanning.

During a helical scan as shown in FIG. 20, since an effective scanning rate approaches zero at a central portion of the specimen, illumination light is irradiated for a prolonged time at the central portion. The central portion therefore has the greatest temperature rise among the entire specimen surface, and the value of the temperature rise is calculated using expression 3.

Figure 28:
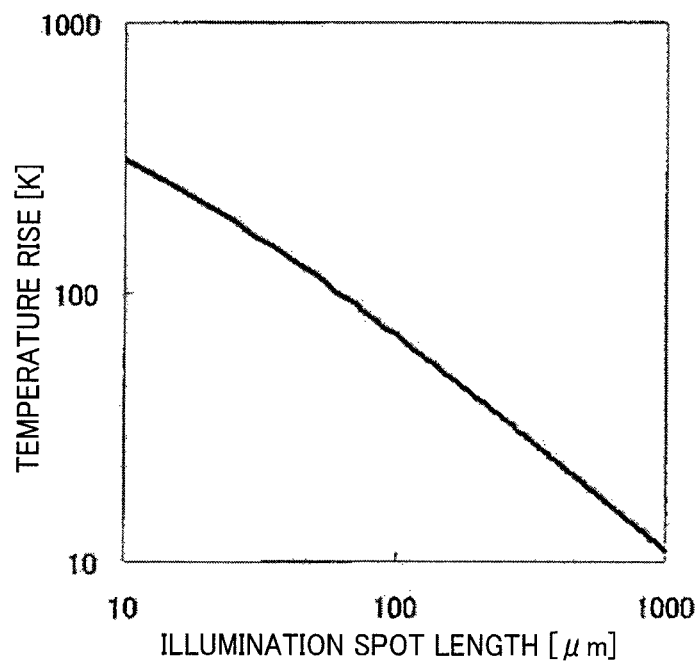
FIG. 28 is a schematic representing a relationship between length of an illumination spot and an increase in specimen surface temperature, in the present invention.
Figure 29:
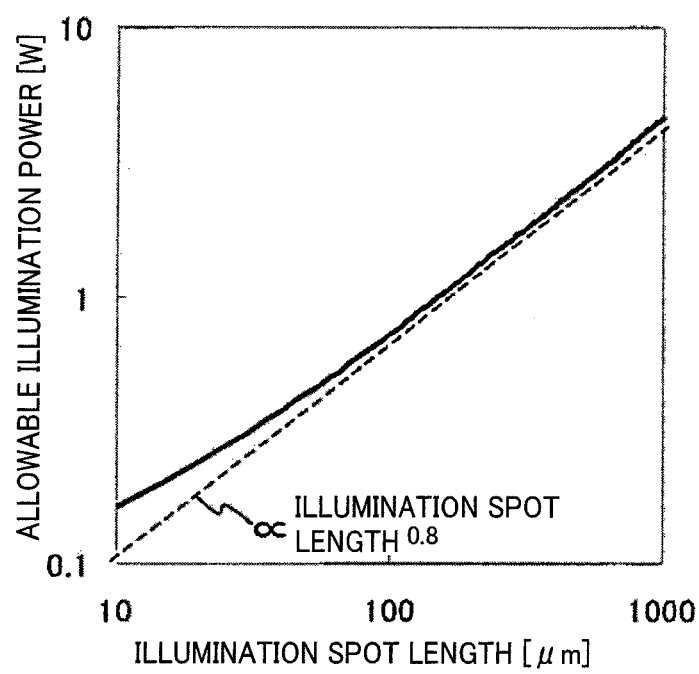
FIG. 29 is a schematic representing a relationship between the length of an illumination spot and allowable illumination power, in the present invention.

Taking a semiconductor silicon wafer as an example of the specimen W, calculation results on the temperature rises at the specimen center are shown in FIGS. 28 and 29. The calculations were conducted with parameters set as $\epsilon$=0.912, $\kappa$=0.000100 [m^2/s], K=168 [W/mK], based on physical characteristics and reflectance of crystalline silicon. FIG. 28 shows calculation results on the temperature rises observed under illumination conditions of P=1 [W], length 2*a* of a short side of the illumination spot 10 [μm], and length 2*b* of a long side of the illumination spot ranging from 10 to 1000 [μm]. FIG. 29 shows calculation results on illumination power level Pc (allowable laser power level) at which a temperature rise does not exceed an allowable temperature rise Tc set tentatively. Deformation of polystyrene, the material of the polystyrene particles commonly used as standard samples in the inspection of foreign materials adhered on semiconductor silicon wafers, occurs at a glass-transition temperature of 100° C. Therefore in the example of FIGS. 28 and 29, Tc=50 [K] (a value such that the silicon surface temperature increases to 75° C. at a room temperature of 25° C.) was set so as not to exceed the glass-transition temperature. FIG. 29 indicates that the allowable illumination power is proportional to approximately 0.8th power of the length of the illumination spot. This relationship does not depend upon the constant value set for Tc since the temperature rise is proportional to the laser power.

According to the relationship between the allowable illumination power and the length of the illumination spot, it is assumed that, for a given illumination spot length L1, an illumination power level P1 is confirmed as the upper limit at which the illumination power causes no damage to the specimen even in the central portion of the specimen. Under other inspection conditions, for instance, when the illumination spot length L1 is doubled (i.e., 2×L1) to double the inspection rate, the maximum allowable illumination power can be found by the following expression.

$$(2^{0.8}) \times P1 = 1.74 \times P1$$

With the use of the relationship between the illumination spot length and the allowable illumination power, an optimal illumination condition for obtaining a maximum amount of scattered light without damaging the specimen can be easily calculated and set.

Figure 30:
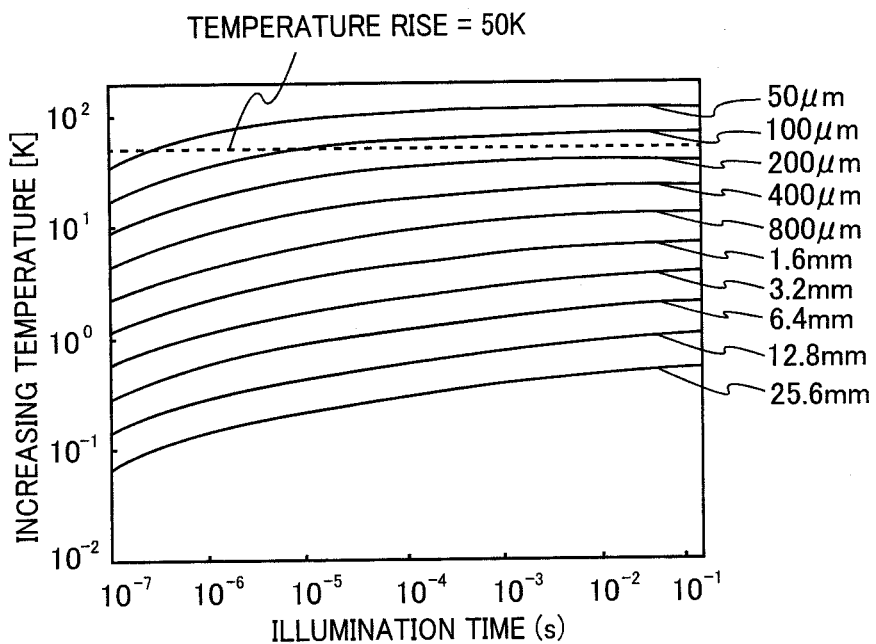
FIG. 30 is a schematic representing a relationship between an illumination light irradiation time and an increase in specimen surface temperature, in the present invention.
Figure 31:
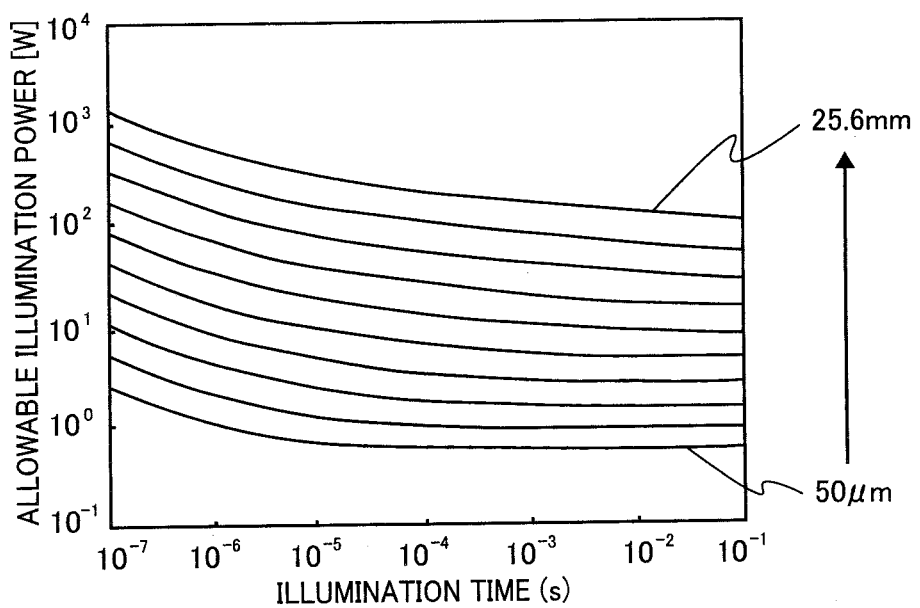
FIG. 31 is a schematic representing a relationship between an illumination light irradiation time and allowable illumination power, in the present invention.

The relationships between illumination light irradiating time and semiconductor silicon wafer temperature rise, derived from expression 1, are shown in FIGS. 30 and 31 per different illumination beam spot lengths. Calculations were conducted assuming that the short side of the illumination spot is 10 μm long. FIG. 31 shows the allowable illumination power for the irradiation time calculated from the results of FIG. 30. The irradiation time is determined by the length of the short side of the illumination spot and the illumination spot scanning rate. In a helical scanning at a constant rotational speed, the irradiation time varies inversely as the distance of the illumination spot position from a rotational center. The maximum allowable illumination power can be calculated using the calculated values shown in FIG. 31, for each different radial position under any illumination condition. Then, based on the thus-calculated maximum value, the attenuator 3 of the illumination unit 101 controls the illumination power according to the particular illumination spot scanning rate. The maximum amount of scattered light can thus be obtained without damaging the specimen.

Figure 21:
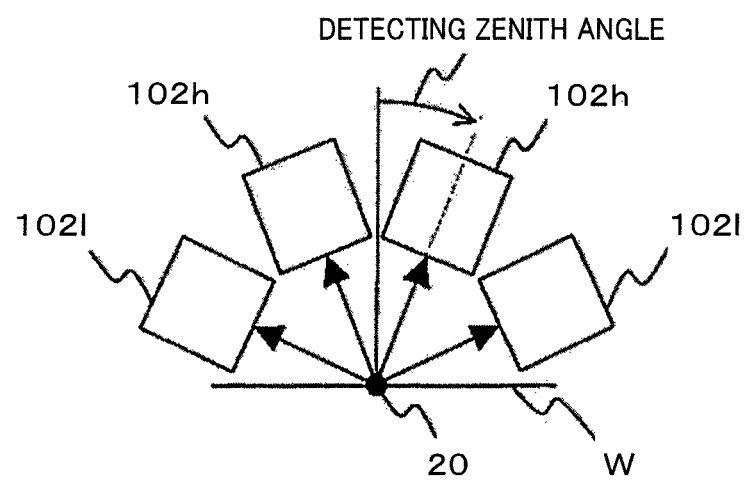
FIG. 21 is a side view that shows layout of detection units and a detection direction according to the present invention.
Figure 22:
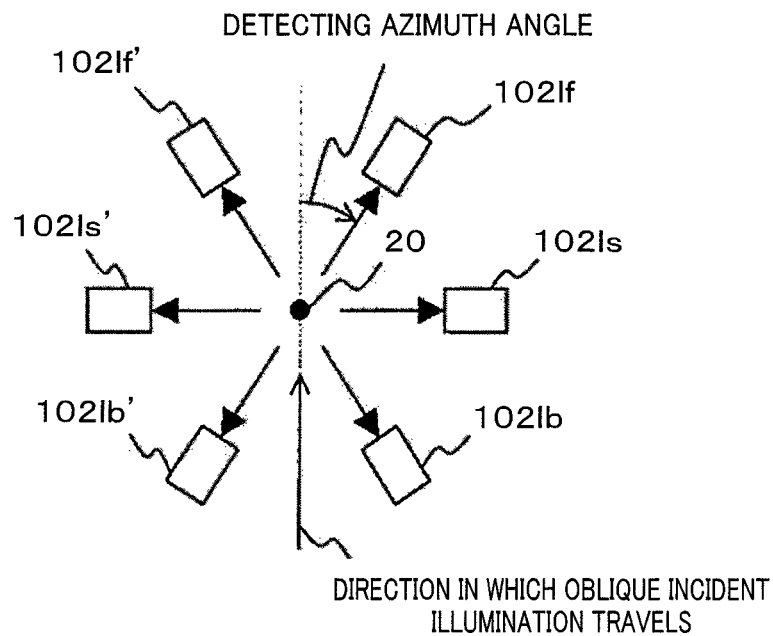
FIG. 22 is a top view that shows layout of low-angle detection units and a detection direction according to the present invention.

A plurality of detection units 102 are disposed to detect scattered lights emitted in a plurality of directions from the illumination spot 20. Examples of arrangement of the detection units 102 with respect to the specimen W and the illumination spot 20 are described below with FIGS. 21 to 23. FIG. 21 shows a side view of the detection units 102. The angle between a normal of the sample and the detection direction (central direction of a detection aperture) of each detection unit 102 forms is defined as a detection zenithal angle. The detection unit 102 consists of, for example, high-angle detection units 102*h* of which detection zenithal angle are less than 45 degrees, and low-angle detection units 102*l* of which detection zenithal angles are 45 degrees or more. The high-angle detection units 102*h* and the low-angle detection units 102*l* each include a plurality of detection units to cover the light scattered in a number of directions at the respective detection zenithal angles. FIG. 22 shows a plan view of the layout of the low-angle detection units 102*l*. The angle formed by the traveling direction and detection direction of off-axis illumination light, in a plane parallel to the surface of the specimen W, is defined as a detection azimuthal angle.

Figure 23:
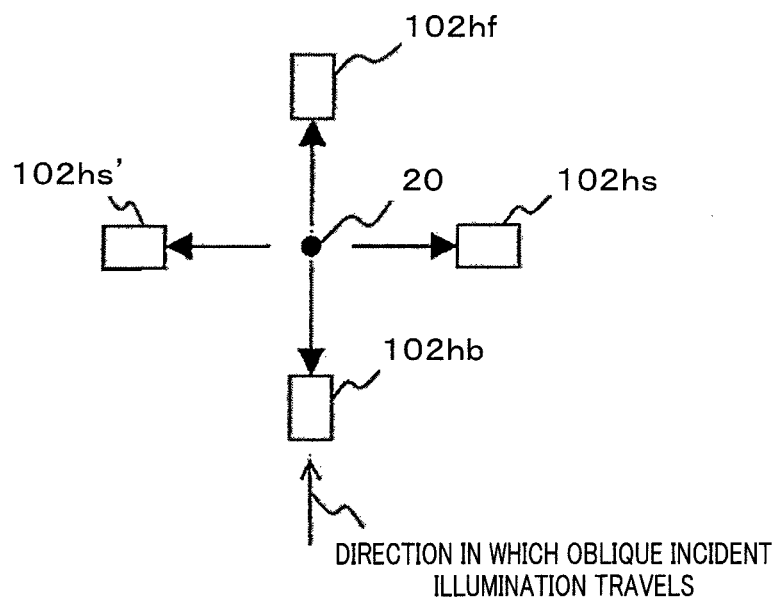
FIG. 23 is a top view that shows layout of high-angle detection units and a detection direction according to the present invention.

Each low-angle detection unit 102*l* includes a low-angle forward detection unit 102*lf*, a low-angle sideways detection unit 102*ls*, and a low-angle backward detection unit 102*lb* as appropriate. The low-angle detection unit 102*l* also includes, as appropriate, a low-angle forward detection unit 102*lf'*, a low-angle sideways detection unit 102*ls'*, and a low-angle backward detection unit 102*lb'*, that are located at symmetrical positions of the former three detection units about an illumination incident plane. For example, detection azimuthal angles of the low-angle forward detection unit 102*lf*, the low-angle sideways detection unit 102*ls*, and the low-angle backward detection unit 102*lb* are respectively 0 to 60 degrees, 60 to 120 degrees, and 120 to 180 degrees. FIG. 23 shows a plan view of the layout of the high-angle detection units 102*h*. Each high-angle detection unit 102*h* includes, as appropriate, a high-angle forward detection unit 102*hf*, a high-angle sideways detection unit 102*hs*, a high-angle backward detection unit 102*hb*, and a high-angle sideways detection unit 102*hs'* located at a symmetrical position with respect to an illumination incident plane of the high-angle sideways detection unit 102*hs*. For example, detection azimuthal angles of the high-angle forward detection unit 102*hf*, the high-angle sideways detection unit 102*hs*, and the high-angle backward detection unit 102*hb* are respectively 0 to 45 degrees, 45 to 135 degrees, and 135 to 180 degrees. Although an example of arranging four high-angle detection units 102*h* and an example of arranging six low-angle detection units 102*l* have been described here, the present invention is not limited to the examples and the number and positions of detection units may be changed as appropriate.

Figure 24:
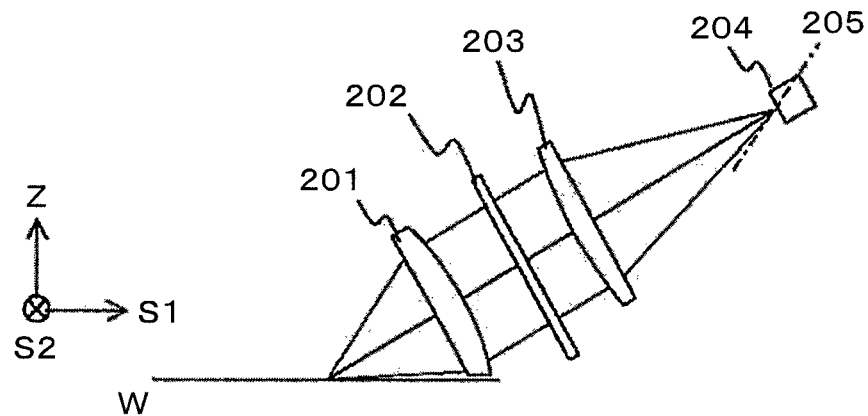
FIG. 24 is a schematic showing a first example of a detection unit configuration according to the present invention.
Figure 25:
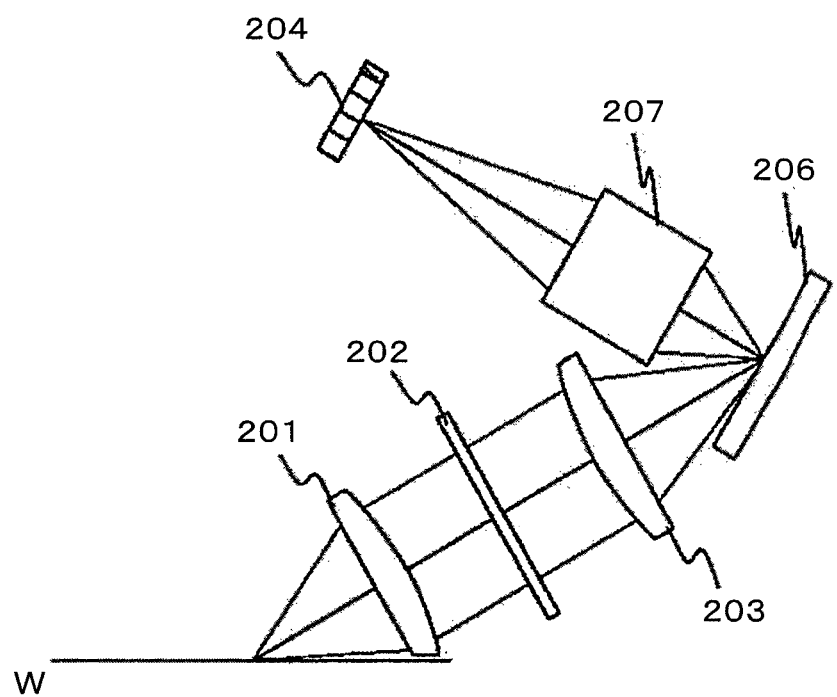
FIG. 25 is a schematic showing a second example of a detection unit configuration according to the present invention.

More specific configurations of the detection unit 102 are shown in FIGS. 24 and 25. FIG. 24 shows a configuration of the low-angle and high-angle sideways detection units 102*ls* and 102*hs* with a detection azimuthal angle of 90-degree. Scattered light that originates from the illumination spot 20 is focused by an objective lens 201, passes through a polarizing filter 202, and then guided by an imaging lens 203 to a light receiving surface of a multi-pixel sensor 204 for detection. The objective lens 201 preferably has a detection NA of at least 0.3 for efficient detection of the scattered light. For low-angle detectors, a lower end of the objective lens 201 is notched as required so that the lower end does not interfere the surface of the specimen W. The polarizing filter 202 includes a polarizer or a polarizing beam splitter and is disposed to cut a component linearly polarized in a certain direction. The polarizer may be a wire grid polarizer with a transmittance of at least 80% for example. As to cut any polarization component including an elliptically polarized component, a polarizing filter including a wave plate and a polarizer is disposed as the polarizing filter 202.

The multi-pixel sensor 204 is a linear array of photodetection pixels. For high-sensitivity detection, this sensor is desirably high in quantum efficiency (at least 30%) and is able to electrically amplify electrons generated by photoelectric conversion. For faster processing, the sensor is desirably capable of reading a plurality of signals in parallel. To ensure a dynamic detection range, the sensor desirably has detection sensitivity (electrical amplification gain) that is easily changeable in a short time using electrical means or the like. Examples of such photodetectors (sensors) are a multi-anode photoelectron multiplier, an avalanche photodiode array, and a linear EMCCD (Electron Multiplying CDD) and a linear EBCCD (Electron Bombardment CDD) capable of reading out signals in parallel.

A configuration using a multi-anode photoelectron multiplier is described in the present example. An image of the specimen surface is formed on a plane 205 conjugate to the specimen surface by the objective lens 201 and the imaging lens 203. Hence this image is inclined with respect to the specimen surface, an image of an object positioning where an image height is high with respect to the scanning direction S1 would be defocused, and therefore blurred and cannot be formed on the beam detection surface of the multiple-pixel sensor 204. Here however, the dimension of the illumination spot 20 in the scanning direction S1 is small so that the object at the position of high image height does not affect detection.

An exemplary configuration of the low-angle and high-angle forward and backward detection units 102*lf*, 102*hf*, 102*lb*, 102*hb* is shown in FIG. 25. Scattered light that originates from the illumination spot 20 is converged by the objective lens 201 and is passed through the polarizing filter 202. Then, the imaging lens 203 forms an intermediate image of the specimen surface on a diffraction grating 206 disposed on a plane conjugate to the specimen surface. The image of the specimen surface that has been formed on the diffraction grating 206 is projected on the beam detection surface of the multi-pixel sensor 204 by image-forming optics 207 and then detected. Considering the shape of the illumination spot elongated in one direction, the multi-pixel sensor 204 is disposed in the plane conjugate to the specimen surface in a manner that alignment of the pixels matches with a longitudinal direction of an image of the illumination spot 20. The diffraction grating 206 diffracts the light guided by the imaging lens 203 to form the intermediate image in a direction normal to the surface of the diffraction grating 206. That is, the diffraction grating has a shape so that an Nth-order diffracted beam of the incident light along the optical axis of the light guided by the imaging lens 203 forms the intermediate image plane in the direction normal to the surface of the diffraction grating 206. A blazed diffraction grating is used to enhance diffraction efficiency. This configuration with the multi-pixel sensor 204 on the plane conjugate to the specimen surface suppresses defocusing in the S1 direction on the specimen surface, resulting in an effective field of view in a broad range. This also allows scattered light to be detected with minimal loss of luminous energy.

When the data calculations shown in FIG. 31 are used to control the illumination power according to the illumination spot scanning rate, the peak values of the scattered light signal will change by the illumination power, even for defects of the same size. For this reason, an applied voltage that determines an electron-multiplying gain of the multiple-pixel sensor 204 in the detection unit 102 is controlled in parallel with the illumination power controlling. The multi-pixel sensor 204 has its dynamic range dynamically suited in association with the control of the illumination power. The voltage to be applied is controlled so that the electron-multiplying gain of the multiple-pixel sensor 204 varies inversely as the illumination power assigned for each illumination spot scanning rate.

A relationship between the length of the illumination spot 20, an optical magnification of the detection unit 102, and a size of the multiple-pixel sensor 204 is described below. For highly sensitive and rapid inspection, the length of the illumination spot 20 is set to approximately 400 μm. When the multi-pixel sensor 204 includes 32 pixels arranged at a pitch of 1 mm, the optical magnification of the detection unit is to be 80 times and the pixels projected on the specimen surface will be pitched at 12.5 μm. When the specimen is rotated at 2,000 rpm under these conditions, the entire surface of the specimen is scanned within 11 seconds in a circular specimen of 300 mm diameter and 17 seconds in circular specimen of 450 mm diameter. For more rapid inspection, the length of the illumination spot 20 is set to approximately 1,000 μm. When the multi-pixel sensor 204 includes 32 pixels arranged at the pitch of 1 mm, the optical magnification required of the detection unit will be 32 times and the pixels projected on the specimen surface will be pitched at 31.3 μm. When the specimen is rotated at 2,000 rpm under these conditions, the entire surface of the specimen will be scanned within 5 seconds in a circular specimen of 300 mm diameter and 7 seconds in a circular specimen of 450 mm diameter.

Figure 26:
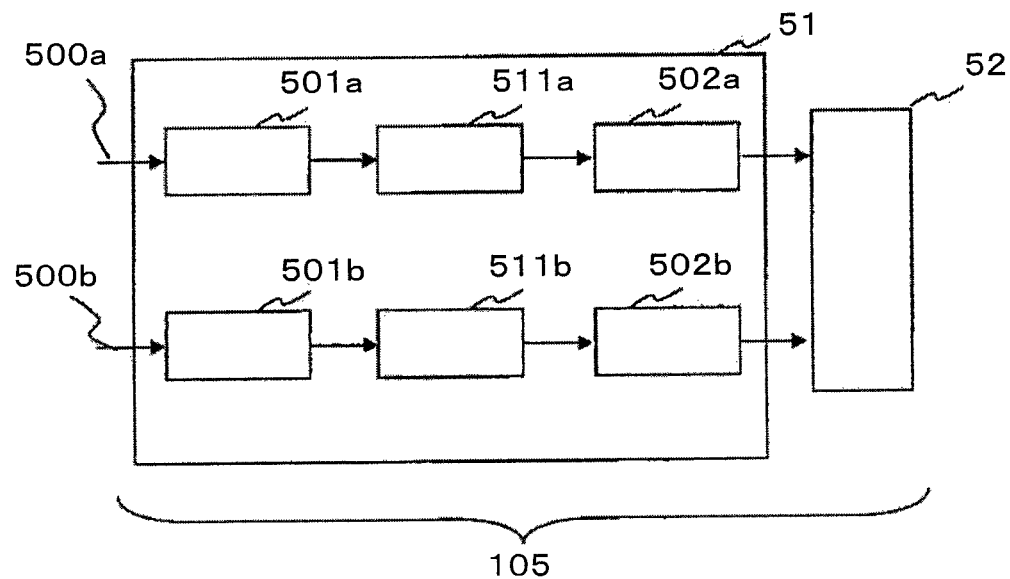
FIG. 26 is a schematic showing an analog processing unit configuration according to the present invention.
Figure 27:
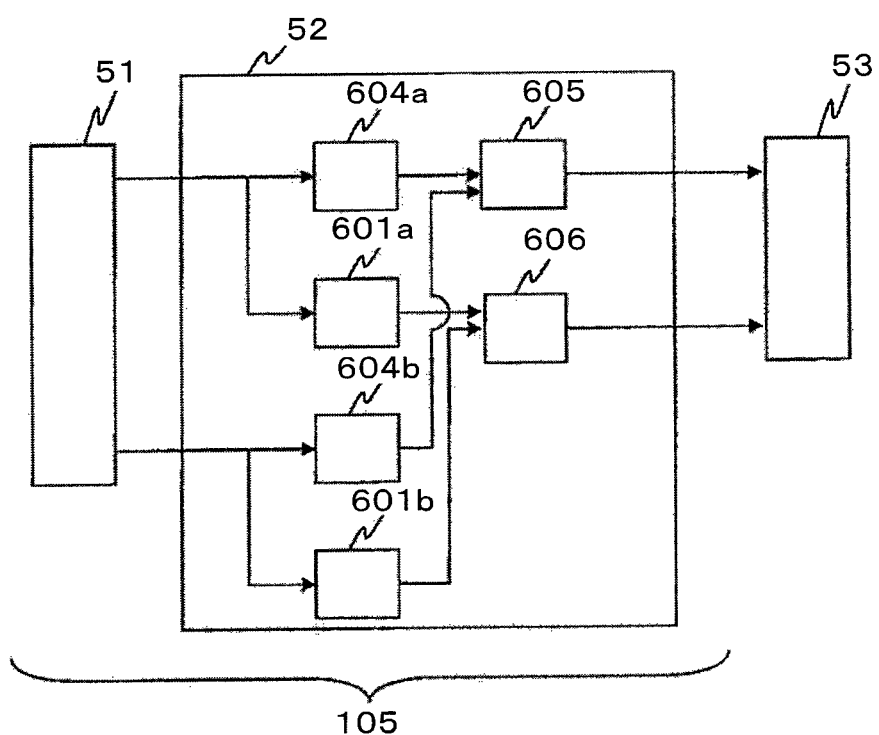
FIG. 27 is a schematic showing a digital processing unit configuration according to the present invention.

Referring to FIGS. 26 and 27, the signal processing unit 105 which accurately classifies various kinds and estimates sizes of the defects is described. The classification and the estimation are based on intensity detection signals of scattered-lights of different directions which are simultaneously detected by the plurality of optical systems covering a wide angle range. The signal processing unit 105 includes an analog processing unit 51 and a digital processing unit 52.

First, the analog processing unit 51 constituting part of the signal processing unit 105 is described below using FIG. 26. For simplicity, the configuration of the analog processing unit 51 described here has only two detection units 102*a* and 102*b* (not shown) among a plurality of detection units 102. Signal currents 500*a* and 500*b* output from detectors provided in the detection units 102*a* and 102*b* are converted into voltages and each amplified by preamplifiers 501*a* and 501*b*. The amplified analog signals are further sent to low-pass filters 511*a* and 511*b*, where the signals then have their high-frequency noise components cut off. The signals are next converted into digital signals by analog-digital converters (A-D converters) 502*a* and 502*b* each provided with a sampling rate higher than a cutoff frequency of each low-pass filter 511*a*, 511*b*. The thus obtained digital signals are output to the digital processing unit 52 provided at the next stage.

Next, the digital processing unit 52 constituting part of the signal processing unit 105 is described below using FIG. 27. In the digital processing unit 52, the output signals from the analog processing unit 51 are sent to high-pass filters 604*a* and 604*b*. Defect signals 603*a* and 603*b* are extracted by the high-pass filters 604*a* and 604*b* and input to a defect determining unit 605. Since defective regions are scanned in an S1 direction by an illumination field 20, each defect signal takes a waveform that is an illuminance distribution profile dimensionally enlarged/reduced in the S1 direction of the illumination field 20. Therefore in the high-pass filters 604*a* and 604*b*, the defect signals are passed through frequency bands including the defect signal waveforms to cut the frequency bands and direct-current components containing a relatively large amount of noise. Accordingly, the defect signals 603a, 603b can be improved in S/N ratio. Each of the high-pass filters 604a, 604b may be a high-pass filter having a specific cutoff frequency and designed to cut off the components of this frequency and higher, or a band-pass filter, or an FIR filter analogous to a waveform of each defect signal that reflects the shape of the illumination spot 20. The defect determining unit 605 conducts threshold processing upon input of the signals output from the high-pass filters 604a, 604b and inclusive of a defect waveform, thereby determining existence of defects. That is to say, the defect determining unit 605 receives defect signals based on the detection signals from the optical systems for detection. The defect determining unit 605 can thus conduct defect inspection with high sensitivity compared to defect detection based on one defect signal by conducting threshold processing to a sum or weighted average of a plurality of defect signals for example. The inspection may be done by conducting OR or AND operations, in one coordinate system set up on the surface of the wafer, between the defect groups that have been extracted during the threshold-based comparisons on the plurality of defect signals.

For the portions determined to have defects, the defect determining unit 605 further calculates estimated values of the defect coordinates representing the in-wafer defect positions and the defect sizes based on the defect waveforms and sensitivity information signals. The estimations are sent to the control unit 53 as defect information and are output to the display unit 54, etc. The defect coordinates are calculated by setting the center of gravity of the defect waveform as a basis. The defect sizes are calculated from an integral value or maximum value of the defect waveform.

Furthermore, the output signals from the analog processing unit 51 are input to the low-pass filters 601a, 601b in addition to the high-pass filters 604a, 604b. The low-frequency components and direct-current components, which correspond to the amount of scattered light (haze) emitted from the microscopic roughness at the illumination spot 20 on the wafer surface, are then output from the low-pass filters 601a, 601b. These outputs from the low-pass filters 601a, 601b are next input to a haze processing unit 606, where haze information processing is conducted. According to the input signal levels obtained from the low-pass filters 601a, 601b, the haze processing unit 606 outputs signals (haze signals) corresponding to the amounts of haze for each location of the wafer. In addition, since an angle distribution of the amount of scattered light from the microscopic roughness varies with a spatial frequency distribution of the roughness, haze signals from each detector of the detection units 102 arranged with different azimuths and angles, as shown in FIGS. 21 to 23, are input to the haze processing unit 606. The haze processing unit 606 can obtain information on the spatial frequency distribution of the microscopic roughness from data such as strength ratios between the haze signals.

Figure 8:
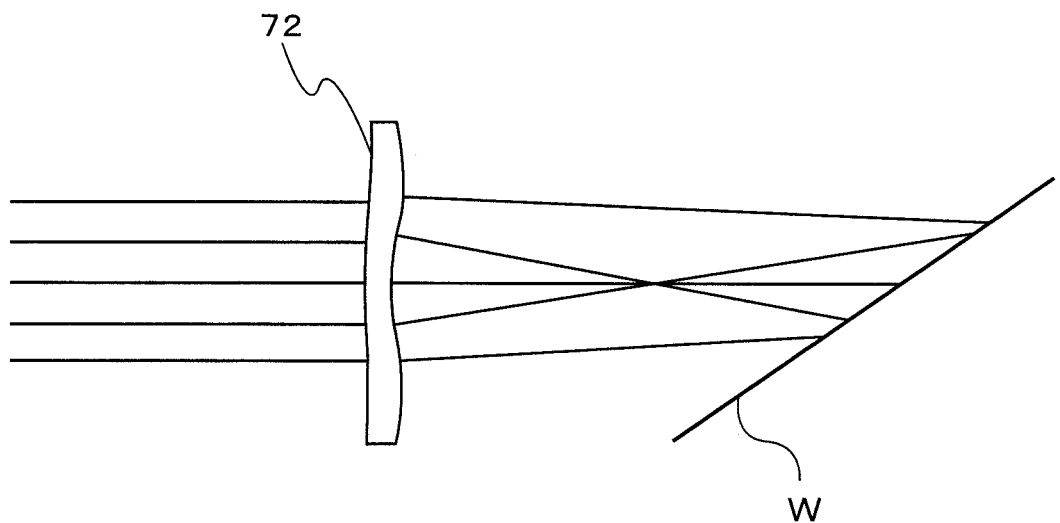
FIG. 8 is a schematic showing a second example of an optical element included in the illumination intensity distribution controller according to the present invention.
Figure 9:
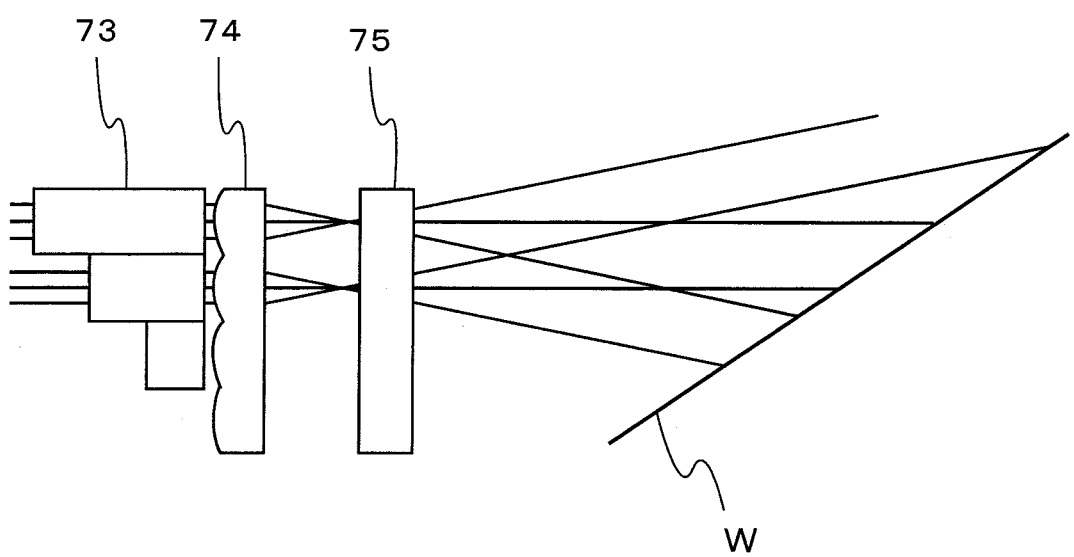
FIG. 9 is a schematic showing a third example of an optical element included in the illumination intensity distribution controller according to the present invention.
Figure 10:
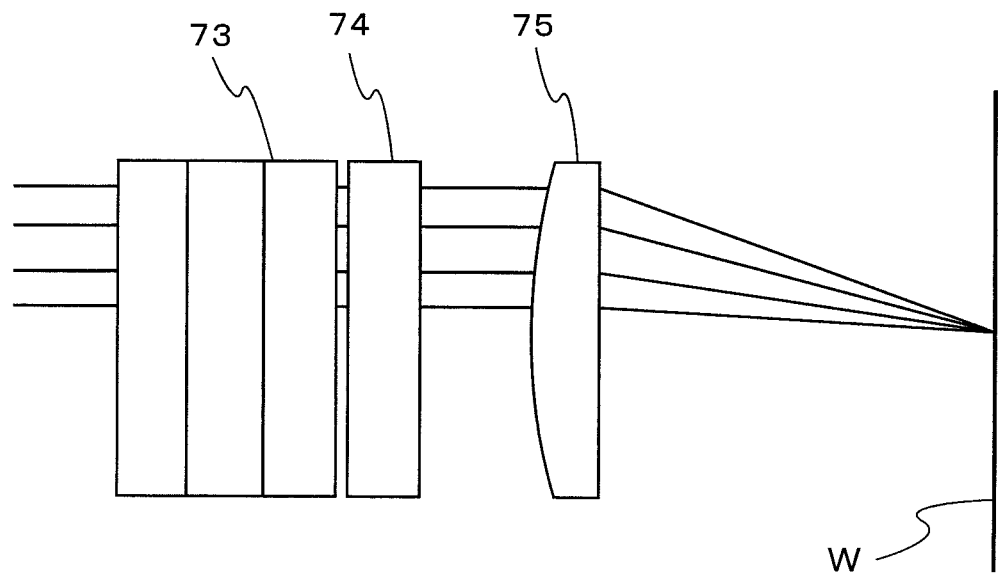
FIG. 10 is a schematic showing a fourth example of an optical element included in the illumination intensity distribution controller according to the present invention.
Figure 11:
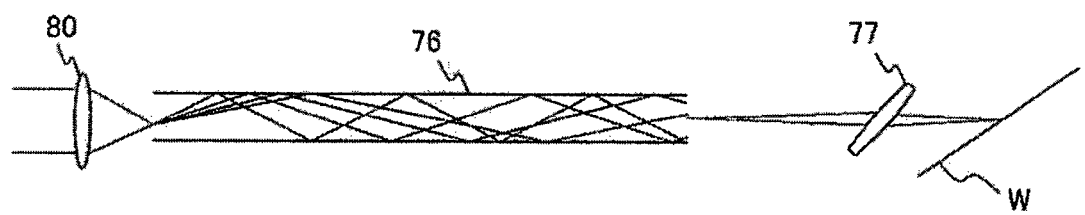
FIG. 11 is a schematic showing a fifth example of an optical element included in the illumination intensity distribution controller according to the present invention.
Figure 12:
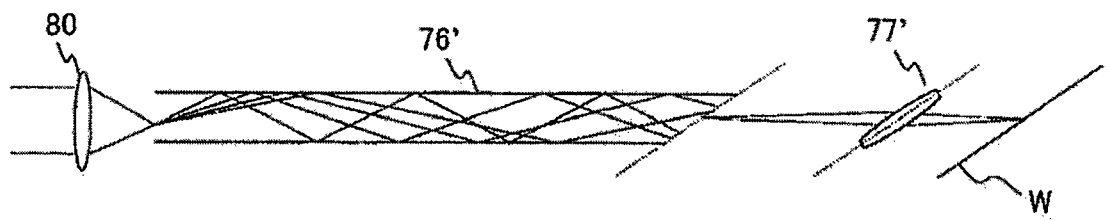
FIG. 12 is a schematic showing a sixth example of an optical element included in the illumination intensity distribution controller according to the present invention.
Figure 13:
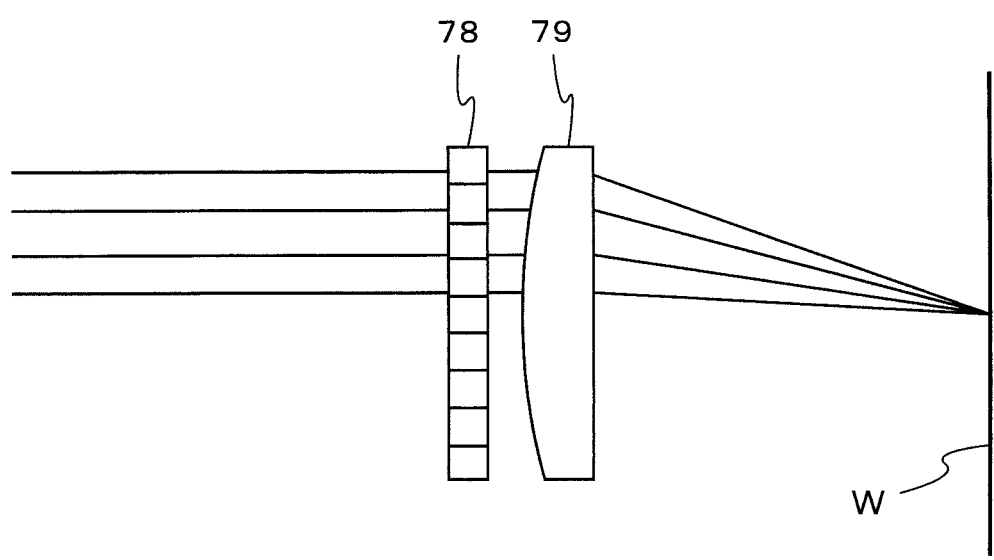
FIG. 13 is a schematic showing a seventh example of an optical element included in the illumination intensity distribution controller according to the present invention.

A modification of an optical element used in the illumination intensity distribution controller 7 is described below. An alternative optical element having substantially the same function as that of the diffractive optical element 71 may be: a non-spherical lens 72 shown in FIG. 8; a combination of a cylindrical lens array 74 and a cylindrical lens 75 shown in FIGS. 9 and 10; a combination of a light pipe 76 and an imaging lens 77 as in FIGS. 11 and 12; or a spatial light modulator (SLM) 78 as in FIG. 13. As shown in FIG. 9, the cylindrical lens array 74 separates a parallel beam of light into a plurality of parallel beams and refracts each of them in the incident plane of the illumination light with respect to the specimen surface. Then the refracted beams are superimposed on the specimen surface. When a laser light source is used as the light source 2, speckling occurs during the superimposition of the illumination beams of light on the specimen surface, thus reducing the uniformity of the illumination intensity distribution. In order to avoid this, optical path difference imparting means 73 formed of stair-like quartz glass blocks or the like is used to impart optical path differences greater than a coherence length of the light source between the plural illumination beams of light. As shown in FIG. 10, in the incident plane of the illumination light with respect to the specimen surface, the parallel incident light passes through the cylindrical lens array 74 while maintaining its parallelism and is focused on the specimen surface by the cylindrical lens 75. The light pipe 76 is a pipe of a cylindrical or prismatic shape. Its wall is formed from a metallic material that reflects illumination light at a high reflectance or the like, and its inside is of an empty space or filled with a material that transmits illumination light at a high transmittance. After the light is converged around an inlet of the light pipe 76 by a condensing lens 80 provided at a preceding stage, the light passes through the inside of the light pipe 76 while repeating reflection for a number of times, and forms a spatially uniform intensity distribution at an outlet of the light pipe 76. The outlet of the light pipe 76 and the specimen surface are interconnected in a conjugate relation by the imaging lens 77. Thus a beam intensity distribution analogous to the uniform beam intensity distribution at the outlet of the light pipe 76 is formed on the specimen surface. As shown in FIG. 11, the imaging lens 77 is inclined with respect to an outlet face and optical axis of the light pipe 76, thereby forming an image of light of the uniform illumination intensity distribution on the specimen surface. Alternatively, a light pipe 76' with an outlet face fabricated parallel to the specimen surface as shown in FIG. 12 may be applied. This enables an optical path between the light pipe outlet plane and the specimen surface to be equidistant regardless of image height, thereby easing the designing of an imaging lens 77'. A spatial light modulator 78 in FIG. 13 controls the illumination intensity distribution on the specimen surface by modulating the intensity or phase of the incident light for each cross section of microscopic regions. Upon receiving a control signal from the control unit 53, the spatial light modulator 78 dynamically controls the illumination intensity distribution on the specimen surface as above. The spatial light modulator 78 may be a liquid-crystal element, a magneto-optic spatial light modulator, a reflective digital micromirror device, or equivalents. A desired illumination intensity distribution is formed using the spatial light modulator 78 alone or in combination with a condenser lens 79.

Figure 33:
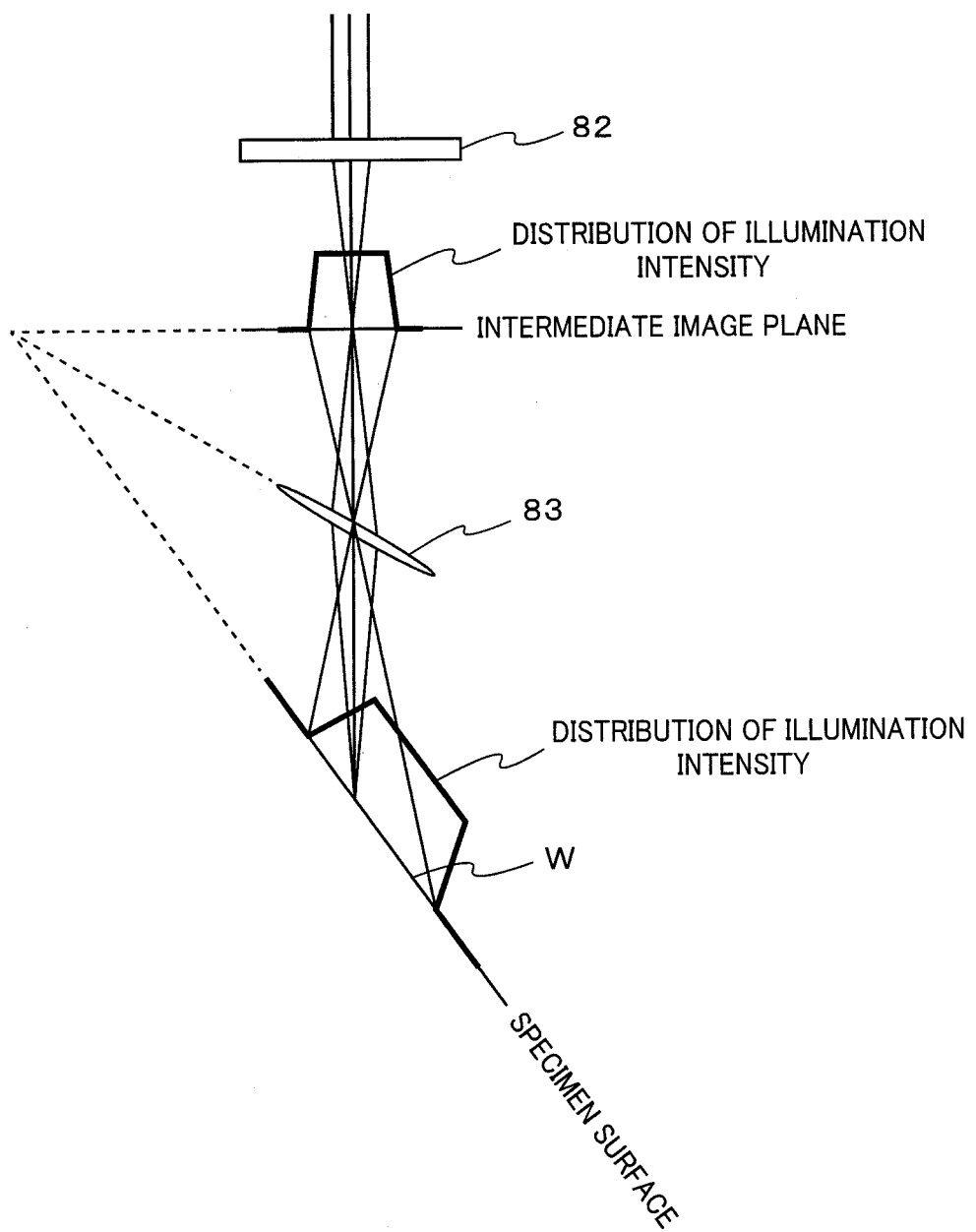
FIG. 33 is a schematic showing an eighth example of an optical element included in the illumination intensity distribution controller according to the present invention.

FIG. 33 shows a configuration of a modification of the illumination intensity distribution controller 7. In this modification, an illumination intensity distribution forming element 82 such as a diffractive optical element forms a predetermined illumination intensity distribution on an intermediate image plane, and the illumination intensity distribution is optically transferred to a specimen surface conjugate to the intermediate image plane via imaging system 83. The illumination intensity distribution forming element 82 that is a diffractive optical element or a non-spherical lens forms a distribution of illumination intensity uniform in one direction. The intermediate image is relayed to and formed on the specimen surface by the imaging system 83. A relationship between the intermediate image plane, a lens surface of the imaging system 83, and the specimen surface, follows the Scheimpflug principle. That is to say, extensions from the three regions cross on one spatial axis (in FIG. 33, at one point). The imaging system 83 includes a plurality of lenses or a non-spherical lens to suppress aberration due to off-axis light and inclination of the specimen surface.

Figure 34:
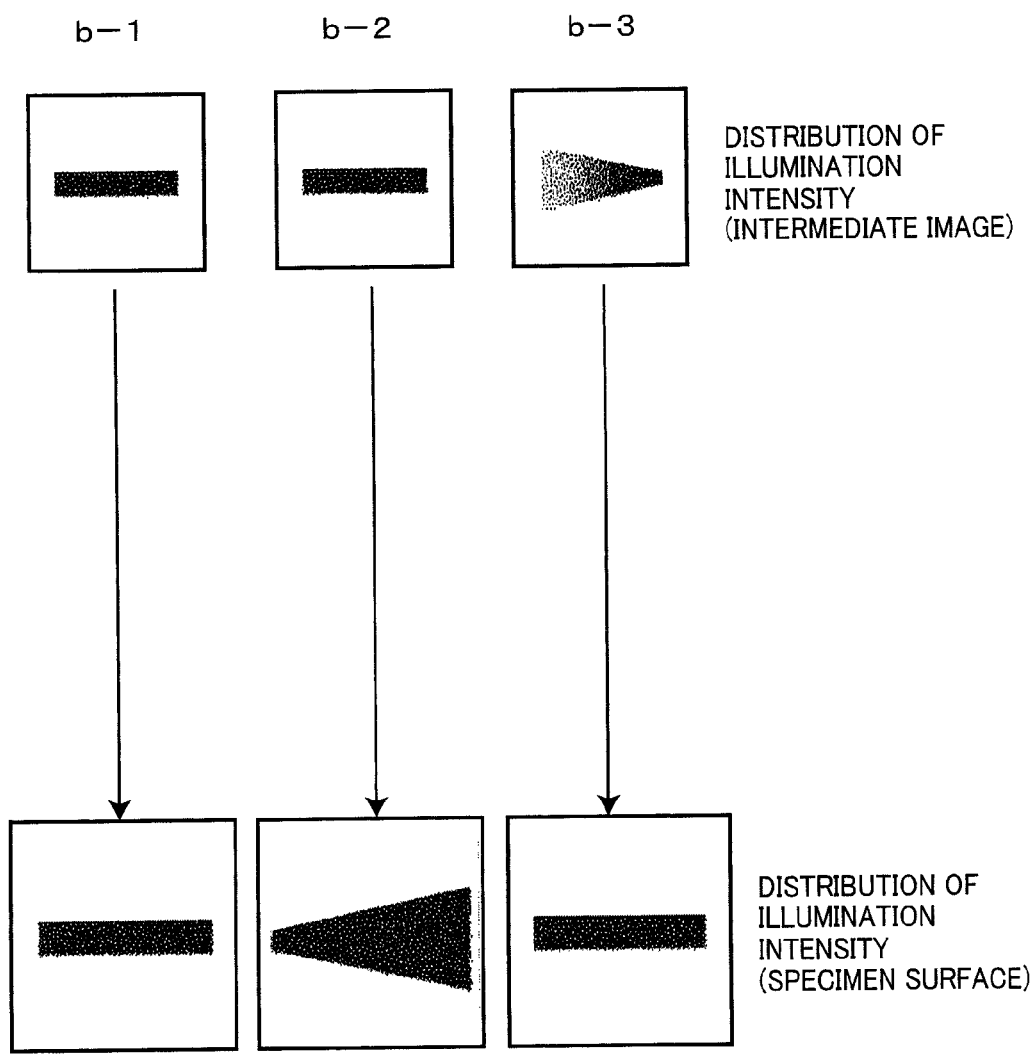
FIG. 34 is a diagram that shows illumination intensity distribution intermediate image and illumination intensity distribution states obtained on the specimen surface by the illumination intensity distribution controller in the eighth example according to the present invention.

In the configuration of FIG. 33, when the intermediate image of the illumination intensity distribution is formed on the specimen surface inclined with respect to the intermediate image plane, the imaging magnification differs according to image height (position on the specimen surface). Thus the rectangular intermediate image changes into a trapezoidal shape as shown in FIG. 34 (b-2). In order to reduce an impact of this deformation, the illumination intensity distribution forming element 82 is predesigned so that the illumination intensity distribution on the intermediate image plane takes a trapezoidal shape facing inversely with the trapezoid shown in FIG. 34 (b-2). This allows formation of a rectangular illumination intensity distribution on the specimen surface as shown in FIG. 34 (b-3). The illumination intensity distribution on the specimen surface can be made uniform by further forming the illumination intensity distribution proportional to an imaging magnification of each image height on the intermediate image plane. In addition, the above-mentioned phenomenon in which a rectangular intermediate image deforms to a trapezoid image is prone to occur in an imaging system 83 with a relatively large angle of view. Therefore, the impact of the deformation can be reduced by configuring the imaging optic 83 to have a small angle of view as shown in FIG. 34 (b-1). More specifically, a visual field size relative to a work distance or focal length of the imaging system 83 is preferably sufficiently small, that is, the ratio between the work distance or focal length and the visual field size is up to 100:1, or the angle of view is up to 10 mrad. For example, if the illumination intensity distribution has a longitudinal size of 1 mm, a desirable work distance of the imaging system 83 is at least 100 mm.

Figure 35:
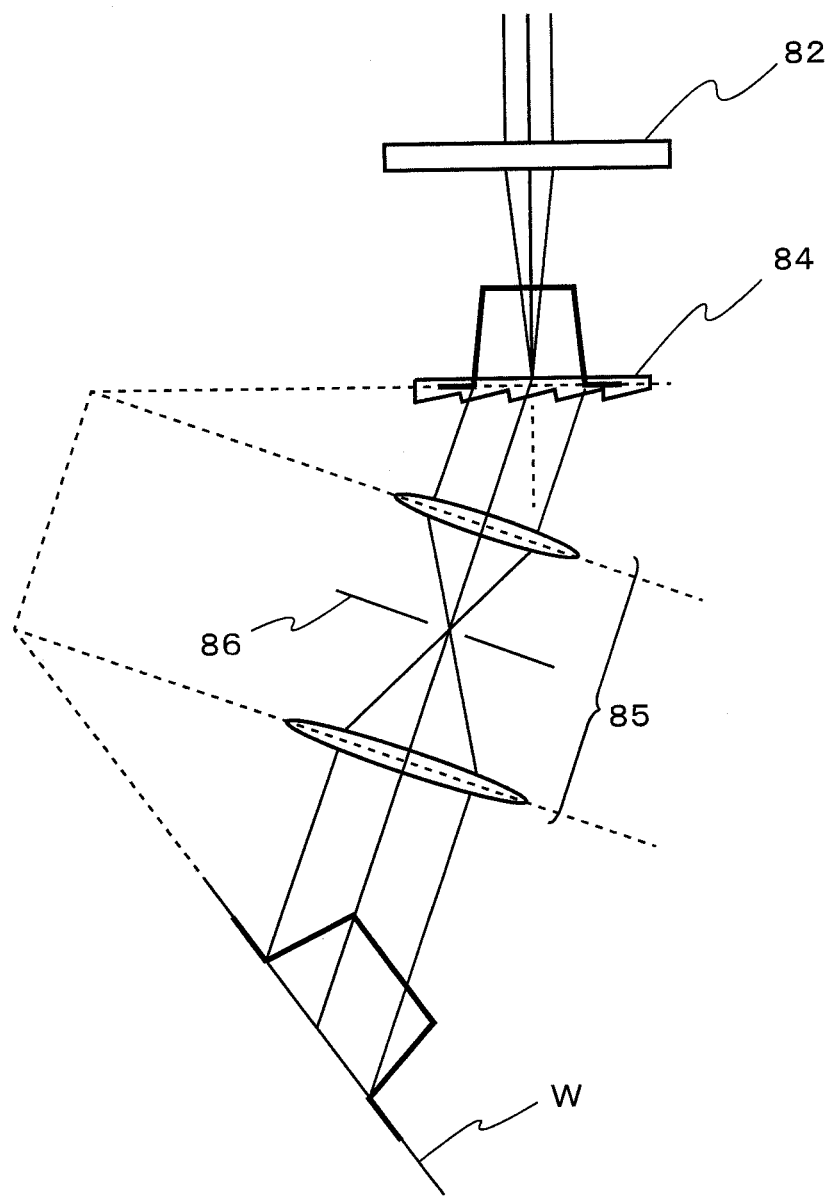
FIG. 35 is a schematic showing a ninth example of an optical element included in the illumination intensity distribution controller according to the present invention.

Another configuration of an example for avoiding the deformation is shown in FIG. 35. A telecentric imaging system 85 is used as an imaging system 83 in this example. An intermediate image of the illumination intensity distribution which has been formed by the illumination intensity distribution forming element 82 is imaged on the specimen surface by the telecentric imaging system 85. The telecentric imaging system 85 is constructed using a plurality of lenses and an aperture diaphragm/stop 86. Constructing the telecentric imaging system 85 in a bilateral telecentric configuration eliminates image height dependence of magnifications and thus suppresses the deformation of the illumination intensity distribution on the specimen surface. In the bilateral telecentric configuration as shown in FIG. 35, the telecentric imaging system 85 has its optical axis inclined with respect to a principal axis of the beam incident on the intermediate image plane. Accordingly, a large condenser NA may be assigned to the telecentric imaging system 85 to cover the principal axis of the beam incident on the intermediate image plane, thereby efficiently guiding light incident on the intermediate image plane to the specimen surface. Alternatively as shown in FIG. 35, a diffraction grating 84 may be placed on the intermediate image plane so that the beam bends after passing therethrough and aligns with the optical axis of the telecentric imaging system 85. A reflective or transmissive blazed diffraction grating is suitable for the diffraction grating 84, and diffraction efficiency in a desired direction will be at least 50% in this case.

Figure 36:
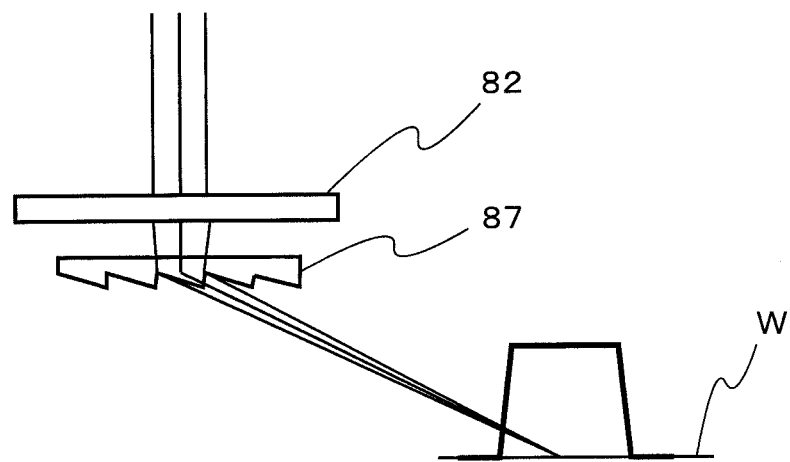
FIG. 36 is a schematic showing a tenth example of an optical element included in the illumination intensity distribution controller according to the present invention.

As another modification of the illumination intensity distribution controller 7, a configuration that uses an illumination intensity distribution forming element 82 and a diffraction grating 87 is shown in FIG. 36. The illumination intensity distribution forming element 82 has a function that forms a desired illumination intensity distribution in a plane perpendicular to the beam axis. The diffraction grating 87 is placed downstream (or in immediate front) of the illumination intensity distribution forming element 82 to bend the beam axis with respect to the wavefront. The desired illumination intensity distribution is formed on the specimen surface inclined with respect to the beam axis. The illumination intensity distribution forming element 82 may be a diffractive optical element or a non-spherical lens. A reflective or transmissive blazed diffraction grating is suitable for the diffraction grating 87, and diffraction efficiency in a desired direction will be at least 50% in this case.

Figure 37:
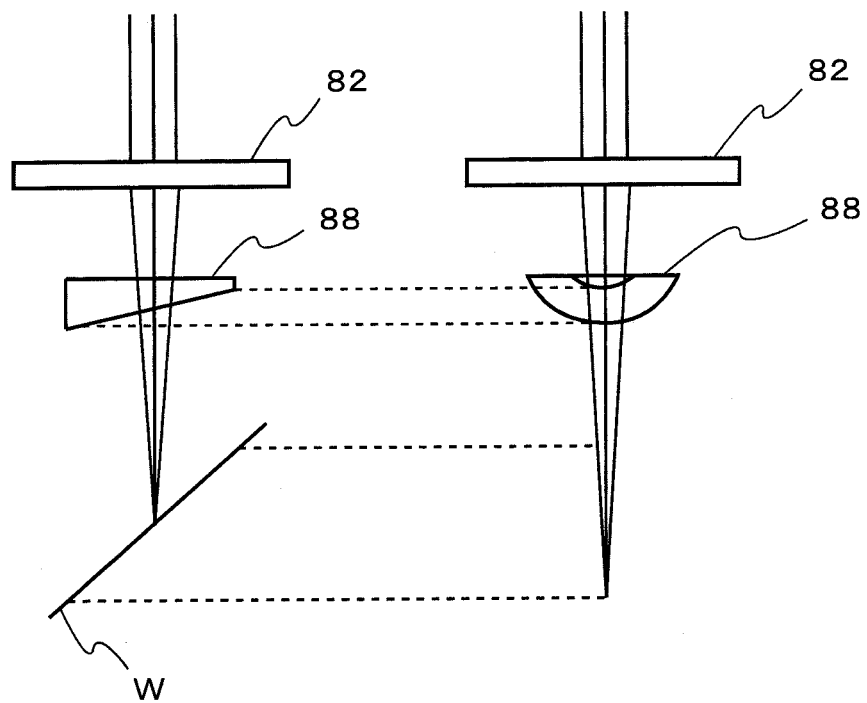
FIG. 37 is a schematic showing an eleventh example of an optical element included in the illumination intensity distribution controller according to the present invention.

As another modification of the illumination intensity distribution controller 7, a configuration that uses the illumination intensity distribution forming element 82 and a conical lens 88 is shown in FIG. 37. The conical lens 88 is a lens that has a conical shape or a lens cut off from a cone of its lateral side, and has a property that the curvature differs according to a position through which the light passes. Matching a direction in which the curvature of the conical lens 88 changes and the incident plane of the beam axis with respect to the specimen surface enables the illumination intensity distribution to be focused on the specimen surface inclined with respect to the beam axis.

Figure 4:
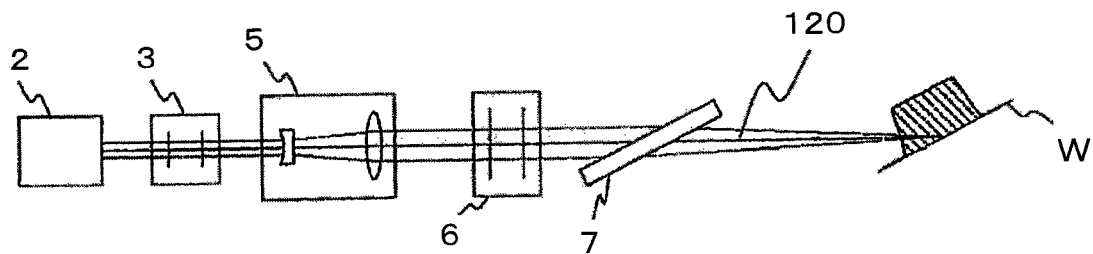
FIG. 4 is a schematic showing a third example of an illumination intensity distribution shape implemented by the illumination unit according to the present invention.

As another modification of the illumination intensity distribution controller 7, an example where an optical element constituting part of the illumination intensity distribution controller 7 is disposed parallel to the specimen surface is shown in FIG. 4. The optical element disposed in this way requires light-condensing performance for focusing off-axis lights significantly inclined to the normal of the optical element surface. Condensing however becomes easy because of the optical element surface and the specimen surface are constantly distanced.

Figure 5:
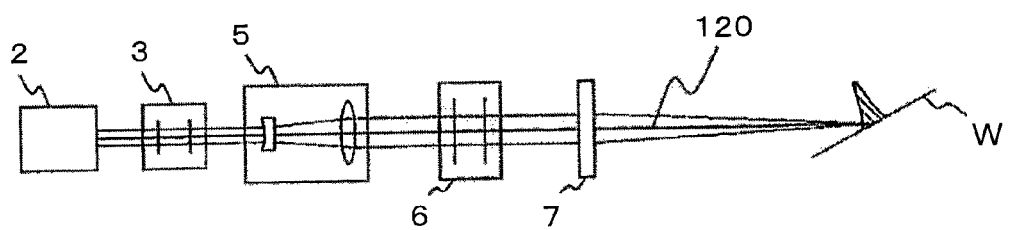
FIG. 5 is a schematic showing a fourth example of an illumination intensity distribution shape implemented by the illumination unit according to the present invention.
Figure 6:
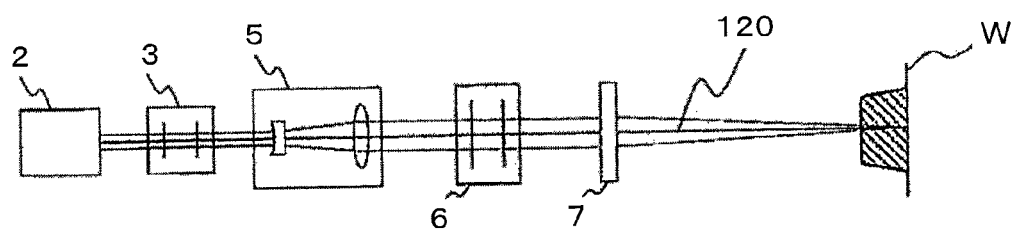
FIG. 6 is a schematic showing a fifth example of an illumination intensity distribution shape implemented by the illumination unit according to the present invention.

Another modification of the illumination intensity distribution controller 7 is shown in FIGS. 5 and 6. In this modification, a uniform illumination intensity distribution is formed on a plane including the normal to the specimen surface and is perpendicular to an incident plane of off-axis illumination light on the specimen surface. The configuration of this modification is advantageous over those of FIGS. 2, 3 in that a uniform illumination intensity distribution is easy to form, hence a uniform illumination intensity distribution is formed on the plane perpendicular to the illumination light axis in this modification. On the other hand, in this modification, a shorter-dimension direction of the illumination spot coincides with a direction of the position deviation of the illumination spot due to a change in specimen surface height. Which causes reduction of coordinate accuracy of the defects detected. To suppress such reduction, the specimen is held by suctioning the whole specimen backside, or slow scanning is conducted at the stage 103.

Figure 18:
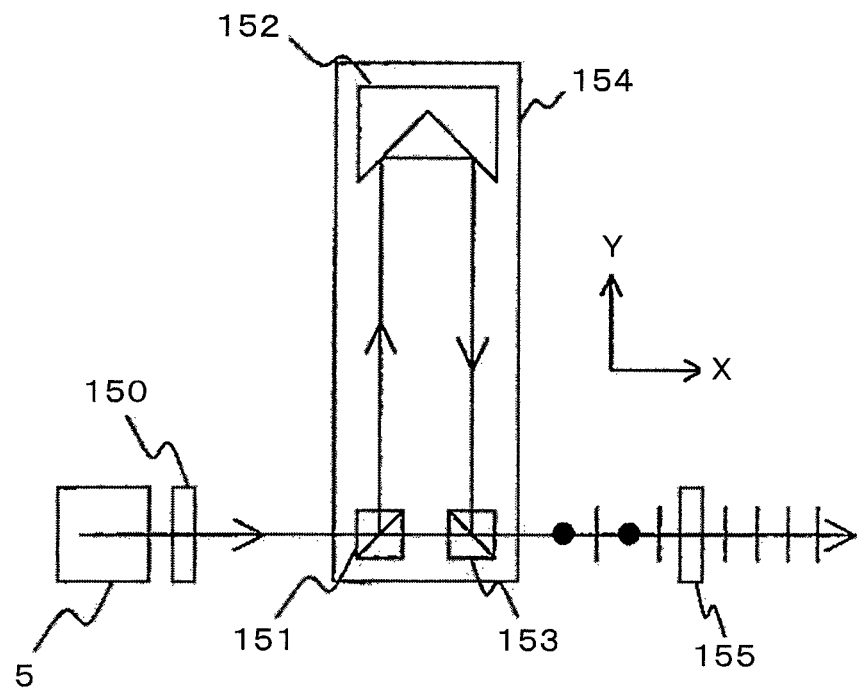
FIG. 18 is a schematic showing a second example of means used to reduce energy per pulse by means of optical path branching and combining in the illumination unit according to the present invention.

A modification of the optical path branching/combining configuration shown in FIG. 16 is described below using FIG. 18. In the configuration of FIG. 16, after an optical path is branched and combined, the polarized light components of two directions that do not interfere with each other are superimposed to make a non-polarized state. As a result, a loss of illumination energy occurs during generation of linearly polarized light by the polarization controller 6 located in the following stage. This modification shown in FIG. 18 employs a polarization modulator 155 that is able to chronologically switch a polarization state of the light transmitting. Polarization state of all pulses can therefore be aligned and linearly polarized light can be generated without losing illumination energy. A photoelastic modulator (PEM), a liquid-crystal element, an electro-optic modulator, an acousto-optic modulator, or the like may be used as the polarization modulator 155.

The present invention scans the entire surface of a specimen within a short time, detects microscopic defects on the surface while reducing thermal damage to the specimen, calculates sizes of the detected defects accurately, and outputs stable inspection results.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description, and all changes which come within the meaning and range of equivalency of the claims are therefore intended to be embraced therein.

REFERENCE SIGNS LIST 2 laser light source
3 attenuator
4 exit beam regulator
5 beam expander
6 polarization controller
7 illumination intensity distribution controller
7v illumination intensity distribution controller
22 beam monitor
23 beam monitor
24 illumination intensity distribution monitor
53 control unit
54 display unit
55 input unit
101 illumination unit
102 detection unit
103 stage
105 signal processing unit
120 optical axis
201 objective lens
202 polarizing filter
203 imaging lens
204 multi-pixel sensor
205 plane conjugate to the specimen surface

The invention claimed is:

1. A defect inspection method, comprising:
regulating illumination light emitted from a light source to be a beam of light having a desired quantity of light, a desired position, a desired beam diameter, and a desired polarization state, by using a regulation unit including an attenuator, exit beam regulator, beam expander, and polarization controller;
guiding the beam obtained in the step of regulating illumination light to a specimen surface at a desired angle of incidence, and controlling an illumination intensity distribution, by using an illumination intensity distribution controller, so that the illumination intensity distribution of light illuminating the surface of the specimen is substantially uniform in a certain direction on the specimen surface;
scanning the specimen, at a position on the specimen surface where the specimen is irradiated with the illumination light in the step of guiding the beam, by moving a stage on which the specimen is mounted, in a direction substantially perpendicular to the direction in which the illumination intensity distribution is substantially uniform;
detecting, with sensors, scattered light emitted from the specimen surface in the specimen scanning step, wherein a plurality of scattered-light components are emitted in a plurality of directions different from each other, and outputting a plurality of scattered-light detection signals from the sensors corresponding to the detected scattered-light components;
determining existence of a defect by using a high-pass filter configured to process at least one of the scattered-light detection signals obtained in the step of detecting scattered-light;
determining a size of the defect with a defect determining unit by processing at least one of the scattered-light detection signals corresponding to sections determined to be defective in the step of determining existence of defect; and
displaying on a display unit, of the section determined to be defective in the step of determining a size of the defect, position on the specimen surface and the defect size obtained in the step of determining a size of the defect;
wherein in the step of regulating illumination light, the quantity of light of the beam is set based on a maximum value of specimen surface temperature rises, calculated by using data of a size of an illumination spot on the specimen surface and a thermal conductivity and a thermal diffusivity of a material of the specimen surface.

2. The defect inspection method according to claim 1, wherein in the step of detecting scattered-light, scattered light emitted from a plurality of sub-regions within a region irradiated with the illumination light in the step of guiding the beam are guided to each of a plurality of photodetection elements and detected.

3. The defect inspection method according to claim 1, wherein the step of regulating illumination light includes a sub-step of measuring a quantity of illumination light and a position of the beam by a beam monitor.

4. The defect inspection method according to claim 3, further comprising: a step of measuring the illumination intensity distribution on the specimen surface, with an illumination intensity distribution monitor, which is measured in the step of measuring a quantity of illumination light.

5. The defect inspection method according to claim 4, wherein in the step of measuring the illumination intensity distribution further including a step of changing a state of the beam in accordance with the measured quantity of light, the position, or a traveling direction of the beam by an illumination intensity distribution controller so that the state of the beam becomes closer to a desired state.

6. The defect inspection method according to claim 1, wherein in the step of regulating illumination light, the regulation unit sets the quantities of light of the beams guided to the specimen surface under a plurality of inspection conditions different from each other to be substantially proportional to a 0.8th power of a longitudinal size of an illumination spot on the specimen surface under each inspection condition.

7. A defect inspection method, comprising:
regulating illumination light emitted from a light source to be a beam of light having a desired quantity of light, a desired position, a desired beam diameter, and a desired polarization state, by using a regulation unit including an attenuator, exit beam regulator, beam expander, and polarization controller;
guiding the beam obtained in the step of regulating illumination light to a specimen surface at a desired angle of incidence, and controlling an illumination intensity distribution, by using an illumination intensity distribution controller, so that the illumination intensity distribution of light illuminating the surface of the specimen is substantially uniform in a certain direction on the specimen surface;
scanning the specimen, at a position on the specimen surface where the specimen is irradiated with the illumination light in the step of guiding the beam, by moving a stage on which the specimen is mounted, in a direction substantially perpendicular to the direction in which the illumination intensity distribution is substantially uniform;

detecting, with sensors, scattered light emitted from the specimen surface in the specimen scanning step, wherein a plurality of scattered-light components are emitted in a plurality of directions different from each other, and outputting a plurality of scattered-light detection signals from the sensors corresponding to the detected scattered-light components;

determining existence of a defect by using a high-pass filter configured to process at least one of the scattered-light detection signals obtained in the step of detecting scattered-light;

determining a size of the defect with a defect determining unit by processing at least one of the scattered-light detection signals corresponding to sections determined to be defective in the step of determining existence of defect; and displaying on a display unit, of the section determined to be defective in the step of determining a size of the defect, position on the specimen surface and the defect size obtained in the step of determining a size of the defect;

wherein in the step of regulating illumination light, the quantity of light of the beam is set based on a size of an illumination spot on the specimen surface, a thermal conductivity and a thermal diffusivity of a material of the specimen surface, and a moving speed of the specimen in the step of scanning the specimen.

8. The defect inspection method according to claim 7, wherein in step of regulating the illumination light regulating step, the quantity of light of the beam is dynamically changed by an attenuator during the movement of the specimen in the step of scanning the specimen.

9. A defect inspection device, comprising:
illumination light regulator configured to regulate illumination light emitted from a light source to be a beam of light having a desired quantity of light, a desired position, a desired beam diameter, and a desired polarization state;

illumination intensity distribution controller configured to guide the beam obtained by the illumination light regulator to a specimen surface at a desired angle of incidence, and configured to control an illumination intensity distribution, so that the illumination intensity distribution of light illuminating the surface of the specimen is substantially uniform in a certain direction on the specimen surface;

specimen scanning unit, at a position on the specimen surface where the illumination intensity distribution controller irradiates the specimen with the illumination light, moving the specimen in a direction substantially perpendicular to the direction in which the illumination intensity distribution is substantially uniform;

scattered-light detector configured to detect, of scattered light emitted from the specimen surface by the illumination of the light having the controlled illumination intensity distribution, a plurality of scattered-light components emitted in a plurality of directions different from each other, and configured to output a plurality of scattered-light detection signals corresponding to the detected scattered-light components;

defect determining unit configured to detect existence of a defect by processing at least one of the scattered-light detection signals obtained in the scattered-light detector;

defect size determining unit configured to determine a size of the defect by processing at least one of the scattered-light detection signals corresponding to the sections determined to be defective in the defect determining unit; and display unit configured to display, of the section determined to be defective, position on the specimen surface and the defect size obtained in the defect size determining unit;

wherein the illumination light regulator is configured to set the quantity of light of the beam in accordance with a maximum value of specimen surface temperature rises, calculated by using data of a size of an illumination spot on the specimen surface, and a thermal conductivity and thermal diffusivity of a material of the specimen surface.

10. The defect inspection device according to claim 9, wherein in the scattered-light detector, scattered light rays emitted from a plurality of sub-regions within a region irradiated with the illumination light by the illumination intensity distribution controller are guided to each of a plurality of photodetection elements and detected.

11. The defect inspection device according to claim 9, wherein the illumination light regulator further includes an illumination light measuring unit configured to measure the quantity of light and the position of the beam.

12. The defect inspection device according to claim 11, wherein the illumination intensity distribution controller further includes an illumination intensity distribution measuring unit configured to measure the illumination intensity distribution on the specimen surface.

13. The defect inspection device according to claim 9, wherein the illumination light regulator is configured to set the quantities of light of the beams guided to the specimen surface under a plurality of inspection conditions different from each other, so that the quantities of light of the beams are each set to be substantially proportional to a 0.8th power of a longitudinal size of an illumination spot on the specimen surface under each inspection condition.

14. A defect inspection device, comprising:
an illumination light regulator configured to regulate illumination light emitted from a light source to be a beam of light having a desired quantity of light, a desired position, a desired beam diameter, and a desired polarization state;

an illumination intensity distribution controller configured to guide the beam obtained by the illumination light regulator to a specimen surface at a desired angle of incidence, and configured to control an illumination intensity distribution, so that the illumination intensity distribution of light illuminating the surface of the specimen is substantially uniform in a certain direction on the specimen surface;

a specimen scanning unit, at a position on the specimen surface where the illumination intensity distribution controller irradiates the specimen with the illumination light, moving the specimen in a direction substantially perpendicular to the direction in which the illumination intensity distribution is substantially uniform;

a scattered-light detector configured to detect, of scattered light emitted from the specimen surface by the illumination of the light having the controlled illumination intensity distribution, a plurality of scattered-light components emitted in a plurality of directions different from each other, and configured to output a plurality of scattered-light detection signals corresponding to the detected scattered-light components;

a defect determining unit configured to detect existence of a defect by processing at least one of the scattered-light detection signals obtained in the scattered-light detector;

a defect size determining unit configured to determine a size of the defect by processing at least one of the scattered-light detection signals corresponding to the sections determined to be defective in the defect determining unit; and a display unit configured to display, of the section determined to be defective, position on the specimen surface and the defect size obtained in the defect size determining unit;

wherein the illumination light regulator is configured to set the quantity of light of the beam in accordance with a size of an illumination spot on the specimen surface, a thermal conductivity and a thermal diffusivity of a material of the specimen surface, and a moving speed of the specimen moved by the specimen scanning unit.

15. The defect inspection device according to claim 14, wherein the illumination light regulator is configured to dynamically change the quantity of light of the beam during the movement of the specimen by the specimen scanning unit.

* * * * *